(12) United States Patent
Tanaka et al.

(10) Patent No.: US 8,404,364 B2
(45) Date of Patent: *Mar. 26, 2013

(54) ORGANIC ELECTROLUMINESCENT ELEMENT, DISPLAY DEVICE AND LIGHTING DEVICE

(75) Inventors: Tatsuo Tanaka, Kanagawa (JP); Hiroshi Kita, Tokyo (JP); Rie Katakura, Tokyo (JP); Hideo Taka, Tokyo (JP)

(73) Assignee: Konica Minolta Holdings, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/285,238

(22) Filed: Oct. 31, 2011

(65) Prior Publication Data

US 2012/0053351 A1   Mar. 1, 2012

Related U.S. Application Data

(63) Continuation of application No. 12/442,540, filed as application No. PCT/JP2008/050504 on Jan. 17, 2008, now Pat. No. 8,114,532.

(30) Foreign Application Priority Data

Jan. 26, 2007   (JP) .................................. 2007-016145

(51) Int. Cl.
*C07F 15/00* (2006.01)
(52) U.S. Cl. ..................... 428/690; 428/917; 428/411.1; 428/336; 257/40; 548/103
(58) Field of Classification Search .................. None
See application file for complete search history.

(56) References Cited

U.S. PATENT DOCUMENTS

| 8,114,532 B2 * | 2/2012 | Tanaka et al. ................. 428/690 |
| 2006/0186413 A1 * | 8/2006 | Sakakura et al. ............... 257/72 |
| 2007/0128466 A1 * | 6/2007 | Nomura et al. ............... 428/690 |

(Continued)

FOREIGN PATENT DOCUMENTS

| CN | 100362006 | 1/2008 |
| JP | 2004530254 | 9/2004 |

(Continued)

*Primary Examiner* — Jennifer Chriss
*Assistant Examiner* — J. L. Yang
(74) *Attorney, Agent, or Firm* — Lucas & Mercanti, LLP

(57) ABSTRACT

Disclosed is an organic electroluminescent device having high external quantum efficiency and long life. Also disclosed are an illuminating device and a display device. The organic electroluminescent device is characterized by containing at least one compound having a partial structure represented by the following general formula (1). [chemical formula 1] (1) In the formula, $R^1$ represents a group (preferably an aromatic hydrocarbon group, an aromatic heterocyclic group, an alkyl group or an alkoxy group) having 4-20 carbon atoms in total and a substituent having a formula weight of 70-350 (preferably an alkyl group or an alkoxy group); $R^2$-$R^4$ independently represent a substituent; n2 represents a number of 0-4; n3 represents a number of 0-2; n4 represents a number of 0-8; and Q represents an atomic group necessary for forming an aromatic hydrocarbon ring or an aromatic heterocyclic ring.

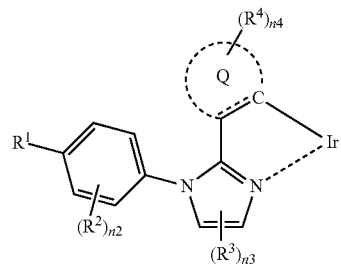

Formula (1)

7 Claims, 2 Drawing Sheets

FOREIGN PATENT DOCUMENTS

WO WO 2004/111037 A1 * 12/2004
WO 2006121811 11/2006
WO WO 2006/121811 A1 * 11/2006

* cited by examiner

ORGANIC ELECTROLUMINESCENT ELEMENT, DISPLAY DEVICE AND LIGHTING DEVICE

This is a Continuation of U.S. application Ser. No. 12/442,540 filed Mar. 24, 2009, which was a National Phase under 35 USC 371 of International Application PCT/JP2008/050504, filed on Jan. 17, 2008, which claimed the priority of Japanese Application No. 2007/016145, filed Jan. 26, 2007, the entire contents of all three applications are hereby incorporated by reference.

TECHNICAL FIELD

The present invention relates to an organic electroluminescent element, a display device and a lighting device.

BACKGROUND

Conventionally, an emission type electronic display device includes an electroluminescence display (hereinafter, referred to as an ELD). A constituent element of an ELD includes such as an inorganic electroluminescent element and an organic electroluminescent element. An inorganic electroluminescent element has been utilized as a flat light source, however, it requires a high voltage of alternating current to operate an emission element. An organic electroluminescent element is an element provided with a constitution comprising an emitting layer containing a emitting substance being sandwiched with a cathode and an anode, and an exciton is generated by an electron and a positive hole being injected into the emitting layer to be recombined, resulting emission utilizing light release (fluorescence•phosphorescence) at the time of deactivation of said exciton; the emission is possible at a voltage of approximately a few to a few tens volts, and an organic electroluminescent element is attracting attention with respect to such as superior viewing angle and high visual recognition due to a self-emission type as well as space saving and portability due to a completely solid element of a thin layer type.

However, in an organic electroluminescent element in view of the future practical application, desired has been development of an organic electroluminescent element which efficiently emits at a high luminance with a low electric consumption.

From this reason, many types of organic electroluminescent elements have been disclosed (for example, refer to Patent Document 1). In the case of utilizing emission from an excited singlet as described above, since a generation ratio of a singlet exciton to a triplet exciton is $1/3$, that is, a generation probability of an emitting exciton species is 25% and a light taking out efficiency is approximately 20%, the limit of an external quantum efficiency ($\eta$ext) of taking out light is said to be 5%.

However, since an organic electroluminescent element which utilizes phosphorescence from an excited triplet has been reported from Princeton University (for example, refer to Non-Patent Document 1), researches on materials exhibiting phosphorescence at room temperature have come to be active (for example, refer to Patent Document 2).

Since the upper limit of internal quantum efficiency becomes 100% by utilization of an excited triplet, which is principally 4 times of the case of an excited singlet, it may be possible to achieve almost the same ability as a cooled cathode ray tube to attract attention also for an illumination application.

For example, many compounds mainly belonging to heavy metal complexes such as iridium complexes have been synthesized and studied (for example, refer to Non-Patent Document 2).

In each case, the luminance of emitted light and the light emission efficiency are considerably improved compared with usual devices since the emitted light is derived from phosphorescence when the light emission device is prepared by the above materials. There is a problem, however, that the lifetime of light emission is shorter than that of the usual devices. As above-mentioned, it is the present condition that the properties applicable to practical use cannot be sufficiently attained yet in the high efficiency phosphorescent light emission material since the wavelength of emitted light is difficultly shifted to shorter side and the light emission lifetime is difficultly improved.

The properties applicable to practical use cannot be sufficiently attained yet in the high efficiency phosphorescent light emission material since the wavelength of emitted light is difficultly shifted to shorter side and the light emission lifetime is difficultly improved.

Besides, metal complexes having phenylpyrrazole as the ligand are known, (for example, refer to Patent Documents 3 and 4). Though the light emission lifetime is improved by the phenylpyrrazole compound having the substituting form of the phenyl group to phenylpyrrazole disclosed here, the improvement is not sufficient and there is still room for improvement from the view point of the light emission efficiency.

On the other hand, it is known that the vacuum vapor deposition method usually applied to production of organic electroluminescent element using a low molecular weight compound causes problems in aspects of the equipment and energy efficiency on the occasion of making large the area of the organic electroluminescent element. Printing methods including an ink-jet method and a screen printing method and coating methods including a spin coat method and a cast coating method are considered preferable. Known phosphorescent emission materials suitable for printing methods or coating methods such as spin coat method and cast coating method are organic metal complexes having a dendrimer portion (for example, refer to Patent Document 5) and organic metal complexes each fixed in a polymer chain (for example, refer to Patent Document 6). However, there is left room to be improved from the viewpoint of the lifetime and efficiency of the light emission.

Patent Document 1: JP-A 3-255190
Patent Document 2: U.S. Pat. No. 6,097,147
Patent Document 3: WO 04/085450
Patent Document 4: JP-A 2005-53912
Patent Document 5: WO 02/066552
Patent Document 6: JP-A 2003-342235
Non-patent Document 1: M. A. Baldo et al., Nature, 395, pp. 151-154, (1998)
Non-patent Document 2: S. Lamansky et al., J. Am. Chem. Soc. 123, p. 4304

DISCLOSURE OF THE INVENTION

Problems to be Solved by the Invention

An object of the present invention is to provide an organic electroluminescent element, display device and lighting device containing a novel compound and having high external quantum efficiency and long lifetime.

Means to Solve the Problems

The above object of the present invention can be attained by the following constitutions.

1. An organic electroluminescent element comprising a compound having a partial structure represented by Formula (1).

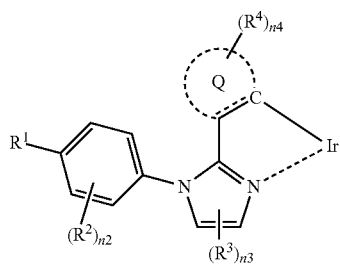

Formula (1)

In the formula, $R^1$ is a group substituted by a substituent having 4 to 20 carbon atoms and a formula weight of from 70 to 350, $R^2$ through $R^4$ are each independently a substituent, n2 is 0 to 4, n3 is 0 to 4 and n4 is 0 to 8. Q is a group of atoms necessary to form an aromatic hydrocarbon ring or an aromatic heterocyclic ring.

2. The organic electroluminescent element described in the above-mentioned item 1, wherein $R^1$ is a group selected from the group consisting of an aromatic hydrocarbon group, an aromatic heterocyclic group, an alkyl group and an alkoxyl group.

3. The organic electroluminescent element described in the above-mentioned items 1 or 2, wherein $R^1$ has an alkyl group or an alkoxyl group each having 4 to 20 carbon atoms.

4. The organic electroluminescent element described in any one of the above-mentioned items 1 to 3, wherein the partial structure represented by Formula (1) is a partial structure represented by Formula (2).

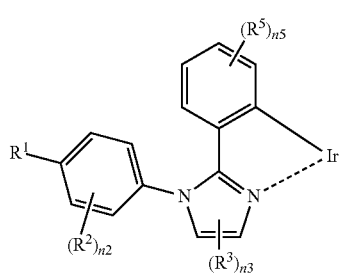

Formula (2)

In the formula, $R^1$, $R^2$ and $R^3$ are each synonymous with $R^1$, $R^2$ and $R^3$ in Formula (1), respectively, $R^5$ is a substituent, n2 and n3 are the same number as n2 and n3 in Formula (1) and n5 is 0 to 4.

5. The organic electroluminescent element described in the above-mentioned item 4, wherein $R^5$ is a group selected from the group consisting of an alkyl group, a cycloalkyl group, an alkenyl group, an alkynyl group, an aromatic hydrocarbon ring group, an aromatic heterocyclic group, a heterocyclic group and an alkoxyl group.

6. The organic electroluminescent element described in any one of the above-mentioned items 1 to 3, wherein the partial structure represented by Formula (1) is a partial structure represented by Formula (3).

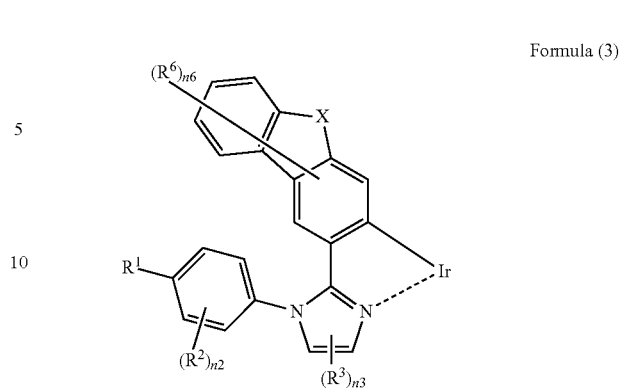

Formula (3)

In the formula, $R^1$, $R^2$ and $R^3$ are each synonymous with $R^1$, $R^2$ and $R^3$ in Formula (1), respectively, $R^6$ is a substituent, n2 and n3 are the same number as n2 and n3 in Formula (1), n6 is 0 to 7 and X is a chalcogen atom.

7. The organic electroluminescent element described in the above-mentioned items 6, wherein $R^5$ is a group selected from the group consisting of an alkyl group, a cycloalkyl group, an alkenyl group, an alkynyl group, an aromatic hydrocarbon ring group, an aromatic heterocyclic group, a heterocyclic group and an alkoxyl group.

8. The organic electroluminescent element comprising an organic layer which contains the compound described in any one of the above-mentioned items 1 to 7.

9. The organic electroluminescent element described in the above-mentioned item 8, wherein the organic layer is a light emitting layer.

10. The organic electroluminescent element described in any one of the above-mentioned items 8 or 9, wherein the organic layer is formed by a wet process.

11. A display device having the organic electroluminescent element described in any one of the above-mentioned items 1 to 10.

12. An lighting device having the organic electroluminescent element described in any one of the above-mentioned items 1 to 10.

Effects of the Invention

Through the present invention, it was achieved to provide an organic electroluminescent element, display device and lighting device containing a novel compound and having high external quantum efficiency and long lifetime.

DESCRIPTION OF SYMBOLS

Figure 1:
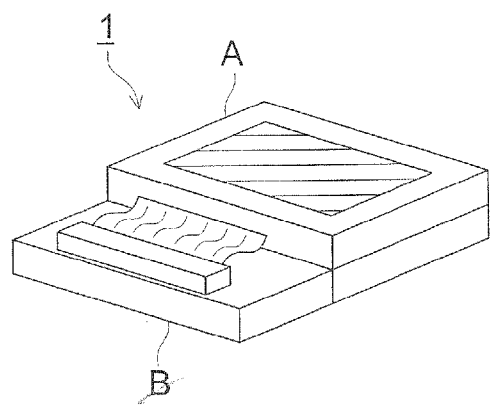
FIG. 1 is a schematic drawing to show an example of a display device constituted of an organic electroluminescent element.

| 1 | display |
| 3 | pixel |
| 5 | scanning line |

-continued

| | |
|---|---|
| 6 | data line |
| 7 | electrical power line |
| 10 | organic electroluminescent element |
| 11 | switching transistor |
| 12 | operating transistor |
| 13 | capacitor |
| A | display section |
| B | control section |
| 107 | glass substrate having a transparent electrode |
| 106 | organic EL layer |
| 105 | cathode |
| 102 | glass cover |
| 108 | nitrogen gas |
| 109 | desiccant |

PREFERRED EMBODIMENTS TO CARRY OUT THE INVENTION

The present invention is described in detail bellow.

In the first place, the compounds of the present invention containing the partial structure represented by Formulas (1), (2) or (3) are described.

<<Compounds Containing the Partial Structure Represented by Formulas (1), (2) or (3)>>

As the aromatic hydrocarbon ring represented by Q in Formula (1), a benzene ring can be cited. The benzene ring may be condensed with an aromatic hydrocarbon ring or the following aromatic heterocyclic ring to form a ring such as a naphthalene ring and a carbazole ring.

As the aromatic heterocyclic ring represented by Q in Formula (1), an oxazole ring, an oxadiazole ring, an oxatriazole ring, an isoxazole ring, a tetrazole ring, a thiadiazole ring, a thiatriazole ring, an isothiazole ring, a thiophene ring, a furan ring, a pyrrole ring, an imidazole ring, a pyrazole ring, a triazole ring, a pyridine ring, a pyridazine ring, a pyrimidine ring, a pyrazine ring, a diazine ring and a triazine ring can be cited.

A benzene ring is particularly preferable as Q in Formula (1).

$R^1$ in Formula (1) represents a group having a carbon atom number of from 4 to 20 in total and a formula weight of from 70 to 350. $R^1$ is preferably a group selected from the group consisting of an aromatic hydrocarbon ring group, an aromatic heterocyclic group, an alkyl group and an alkoxyl group.

As the aromatic hydrocarbon ring group (also called as an aromatic carbon ring group or an aryl group), a phenyl group, a p-chlorophenyl group, a mesityl group, a tolyl group, a xylyl group, a naphthyl group, an anthoryl group, an azulenyl group, an acenaphthenyl group, a fluorenyl group, a phenanthoryl group, an indenyl group, a pyrrenyl group, a biphenylyl group and a methaterphenyl group can be exemplified and the phenyl group is preferable.

As the aromatic heterocyclic group, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolyl group, a carbazolyl group, a carbolinyl group, a diazacarbazolyl (one formed by replacing one optional carbon atom constituting the carboline ring of the carbolinyl group by a nitrogen atom), a phthalazinyl group and a diazacarbazolyl group can be exemplified, and the carbazolyl group is preferable.

As the alkyl group, a methyl group and an ethyl group can be cited and the methyl group is preferable.

As the alkoxyl group, a methoxy group and an ethoxy group are cited, and the methoxy group is preferable.

As the alkyl group having a total carbon number of from 4 to 20 and a formula weight of from 70 to 350, a hexyl group, an octyl group, a dodecyl group, a tridecyl group, a tetradecyl group and a pentadecyl group can be cited, which may have a branched or straight structure. Moreover the alkyl group may be an alkyl group having a total number of carbon atoms which are bonded through a hetero atom of from 4 to 20 and a formula weight of from 70 to 350 such as a di-trimethylsilylmethyl group.

As the alkoxyl group having a total carbon number of from 4 to 20 and a formula weight of from 70 to 350, a hexyloxy group, an octyloxy group, and a dodecyloxy group can be cited, which may have a branched or straight structure. Moreover the alkoxyl group may be an alkoxyl group having a total number of carbon atoms bonding through a hetero atom of from 4 to 20 and a formula weight of from 70 to 350 such as a 1,3,5-trioxanone group.

In Formula (A), examples of the substituents represented by A1 and A2 each include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group, and a cyclohexyl group); an alkenyl group (for example, a vinyl group, an allyl group, a 1-propenyl group, a 2-butenyl group, a 1,3-butadienyl group, a 2-pentenyl group, and an isopropenyl group); an alkynyl group (for example, an ethynyl group and a propargyl group); an aromatic hydrocarbon ring group (also called an aromatic carbon ring or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenyryl group); an aromatic heterocyclic group (for example, a furyl group, a thienyl group, a pyridyl group, a pyridazinyl group, a pyrimidinyl group, a pyrazinyl group, a triazinyl group, an imidazolyl group, a pyrazolyl group, a thiazolyl group, a quinazolinyl group, a carbazolyl group, a carbolynyl group; a diazacarbazolyl group (which is a group in which one of the carbon atoms constituting the carboline ring of the above carbolynyl group is replaced with a nitrogen atom), a phtharadinyl group; a heterocyclic group (for example, a pyrrolidyl group, an imidazolidyl group, a morpholyl group, and an oxazilidyl group); an alkoxy group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, a hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl gropup, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-oyridylaminoureido group); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group, an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a cyano group; a nitro group; a hydroxyl group; a mercapto group; a silyl group (for example, a trimethylsilyl group, a triisopropylsilyl group, a triphenylsilyl group, and a phenyldiethylsilyl group), and a phosphono group.

These substituents may be further substituted by the above substituents. A plurality of the substituents may form a ring by bonding with each other.

In Formula (1), n2 is 0 to 4 and preferably 0 or 1, n3 is 0 to 2 and preferably 0 and n4 is 0 to 8 and preferably 0 or 1.

In Formula (2), $R^1$, $R^2$ and $R^3$ are each synonymous with the group represented by $R^1$, $R^2$ and $R^3$ in Formula (1), respectively, and n2 and n3 each represent the same number as that represented by n2 and n3 in Formula (1).

$R^5$ represents a substituent which is synonymous with the group described as to $R^1$, $R^2$ and $R^3$ in Formula (1), and n5 is 0 to 4 and preferably 0 or 1.

In Formula (3), $R^1$, $R^2$ and $R^3$ each represents the groups synonymous with those represented by $R^1$, $R^2$ and $R^3$ in Formula (1) and n2 and n3 each represents the same number as that represented by n2 and n3 in Formula (1).

$R^6$ represents a substituent synonymous with the group described as to $R^1$, $R^2$ and $R^3$ in Formula (1), and n6 is 0 to 7 and preferably 0 or 1.

The compound of the present invention having the partial structure represented by Formulas (1), (2) or (3) is expanded in planar and spatial direction. As a result of that, effects of that the film forming ability is improved and the concentration quenching is inhibited by the spatial expansion so that the host-free can be attained.

Concrete examples of the compound containing the partial structure represented by any one of Formulas (1), (2) and (3) are shown below. However, the present invention is not limited to them.

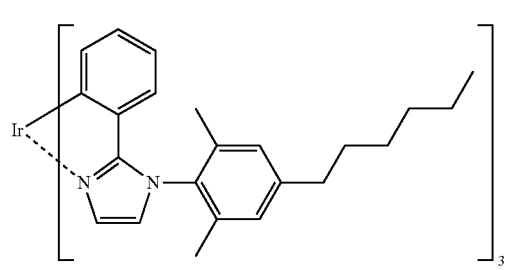

1-1

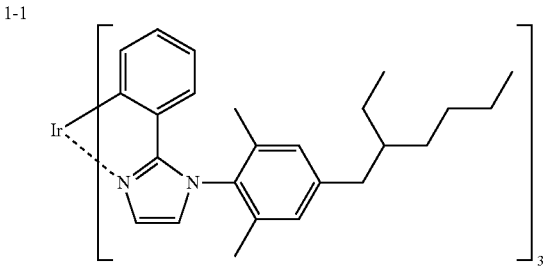

1-2

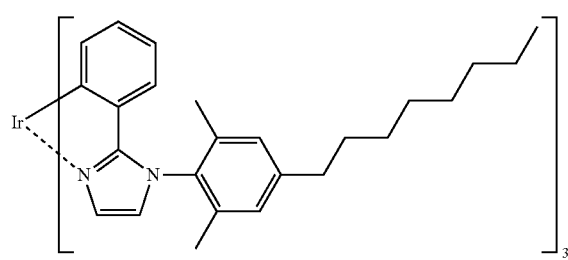

1-3

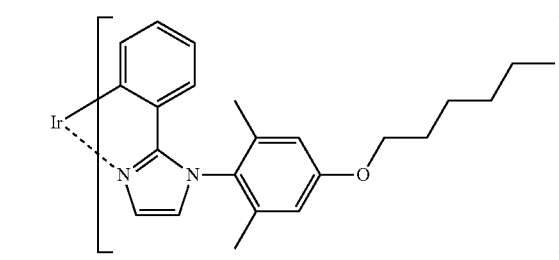

1-4

-continued
1-5
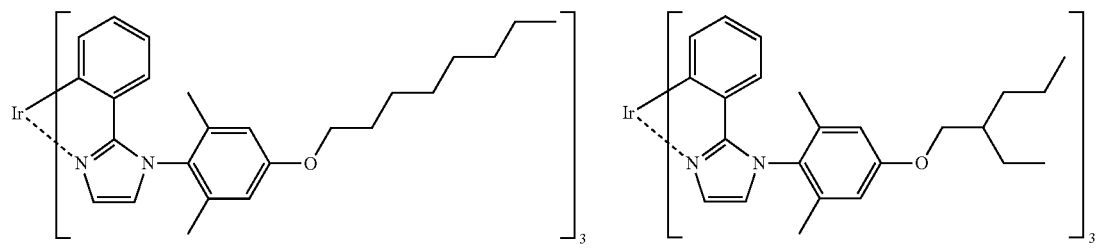
1-6
1-7
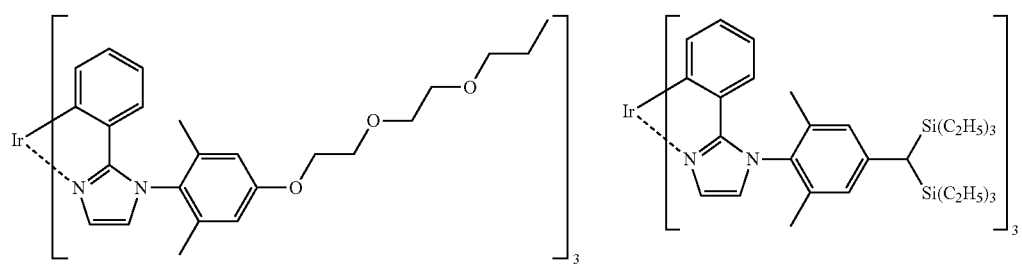
1-8
1-9
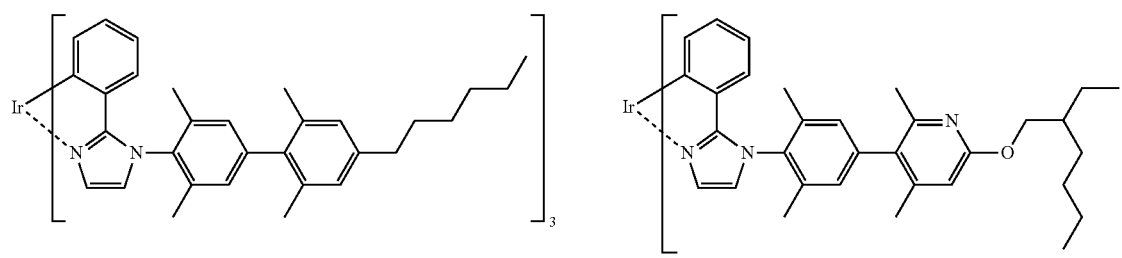
1-10
1-11
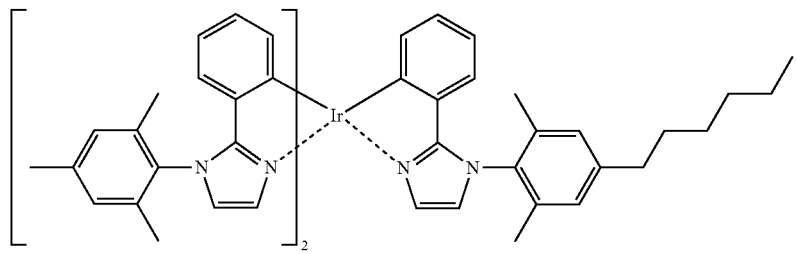
1-12
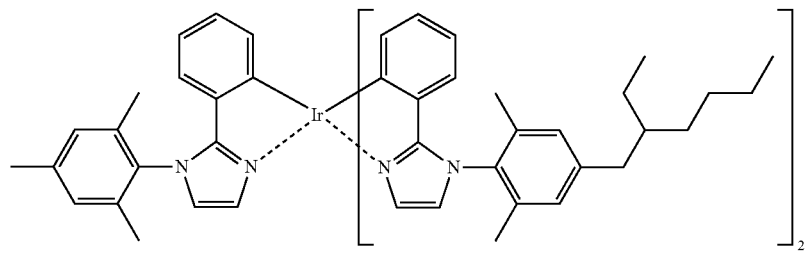
1-13
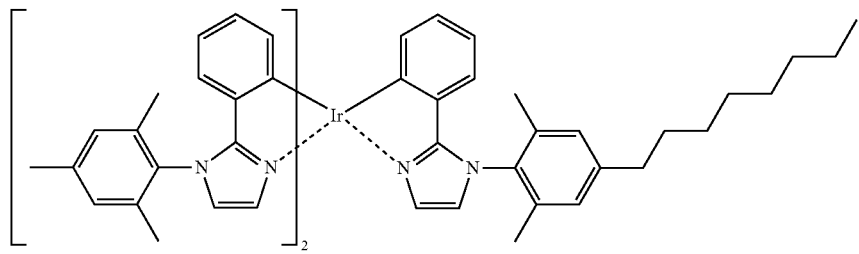

-continued
1-14
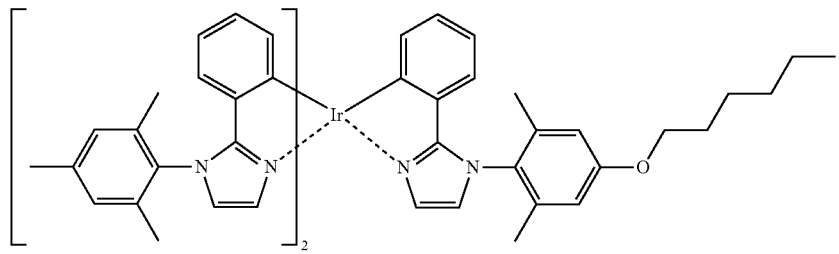
1-15
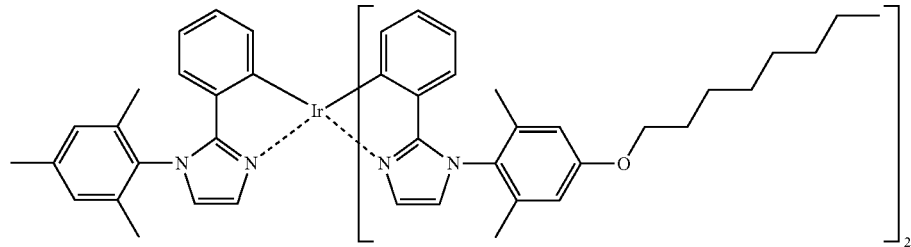
1-16
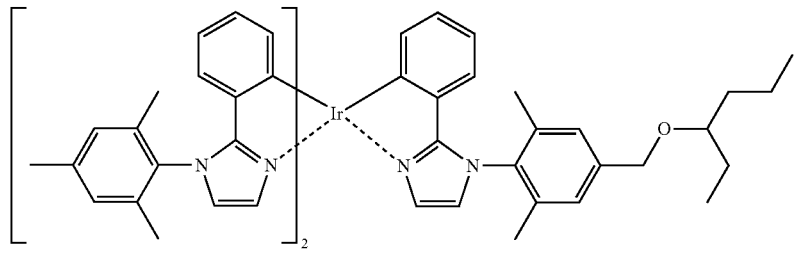
1-17
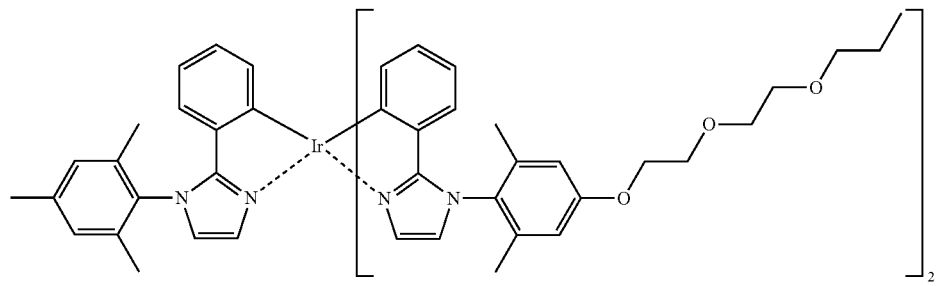
1-18
1-19
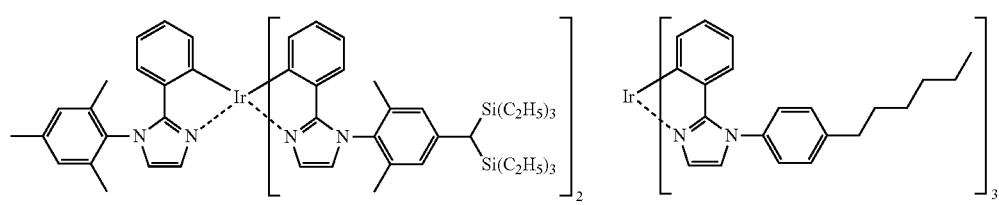
1-20
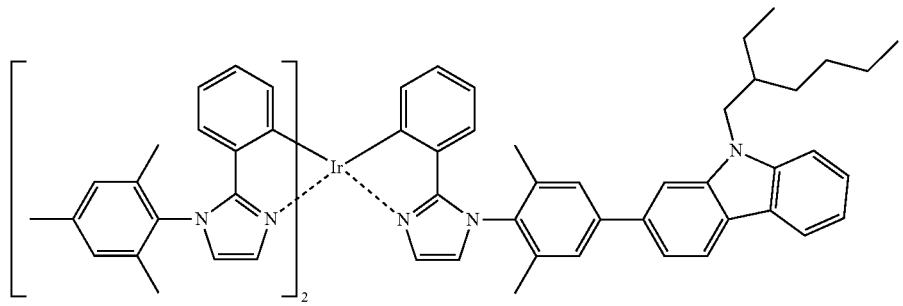

-continued
1-22
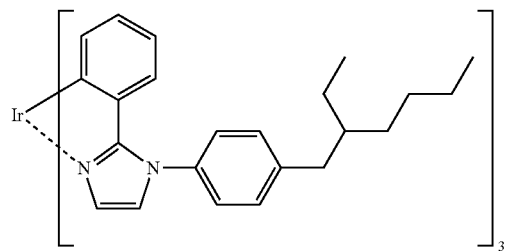
1-23
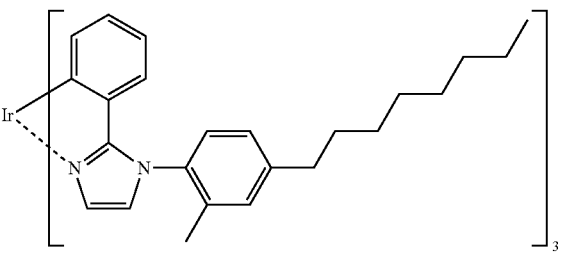
1-24
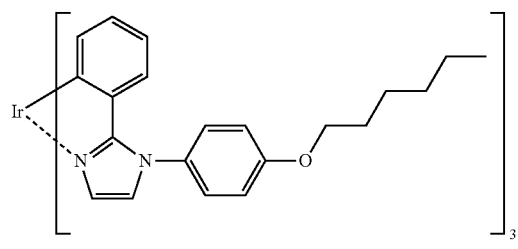
1-25
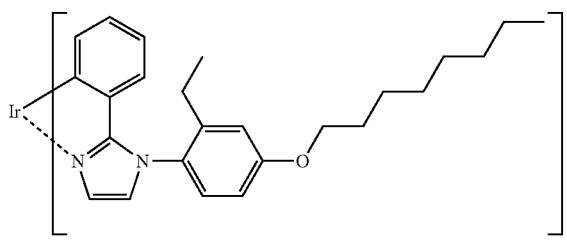
1-26
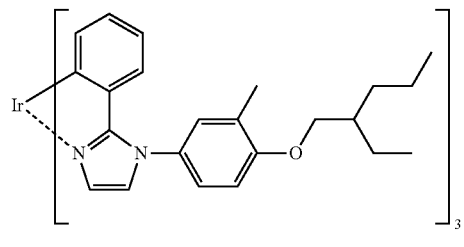
1-27
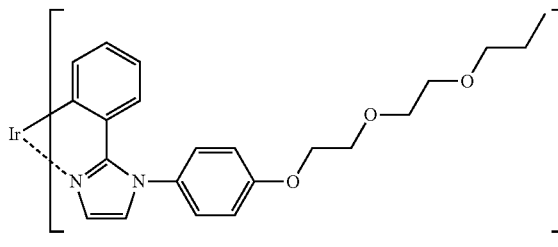
1-28
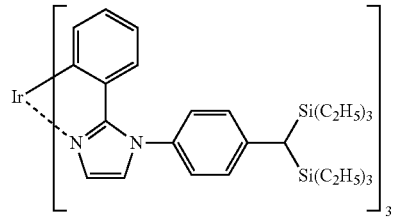
1-29
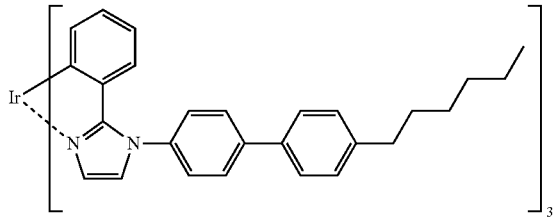
1-30
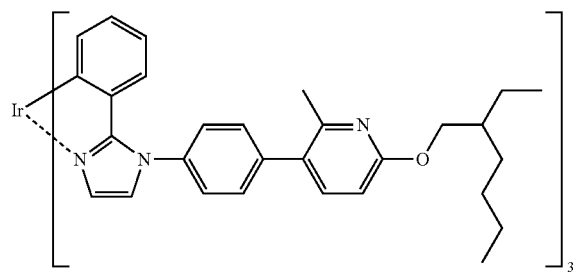
1-31
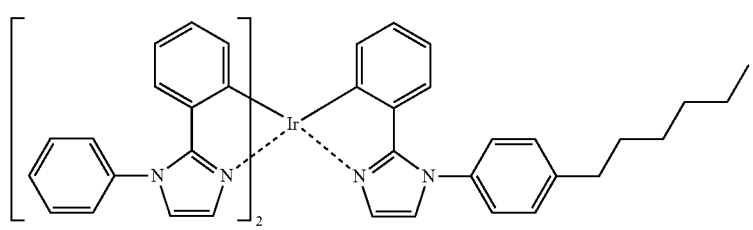

1-32
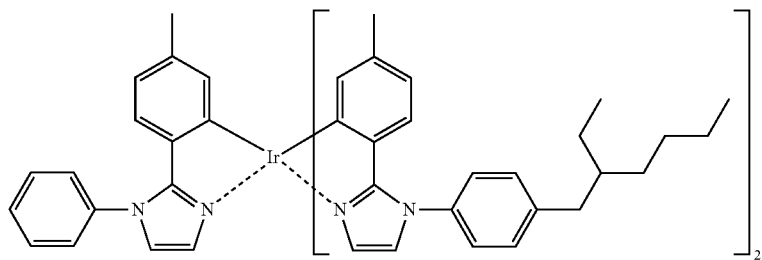
1-33
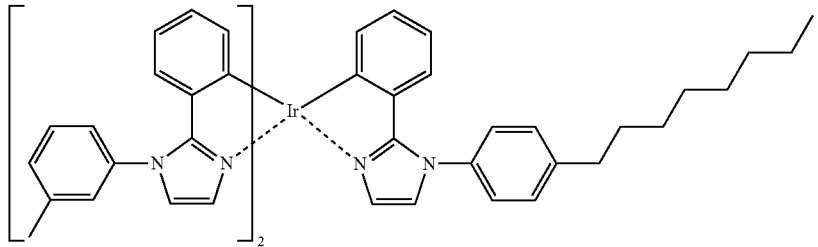
1-34
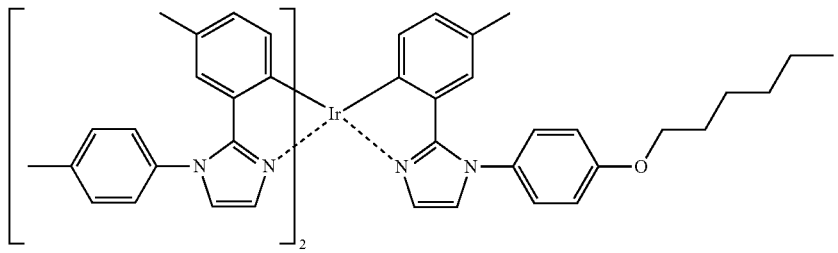
1-35
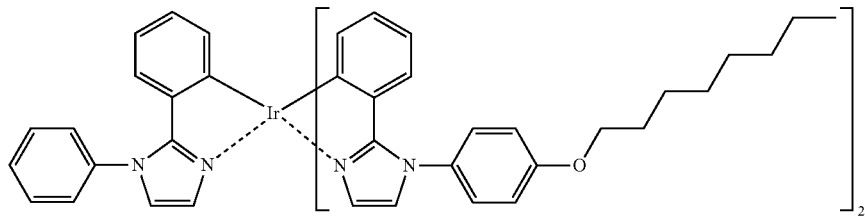
1-36
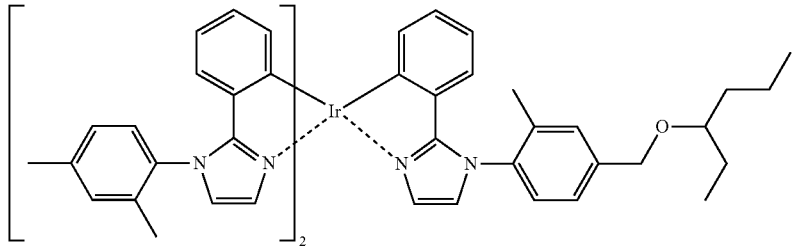
1-37
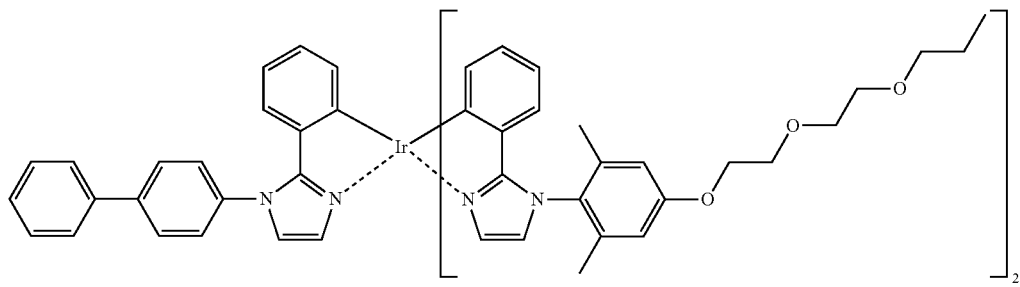

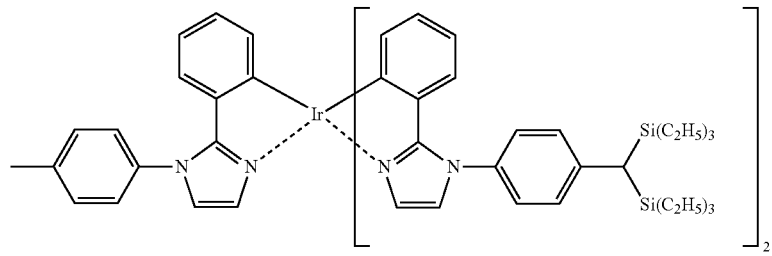
1-38
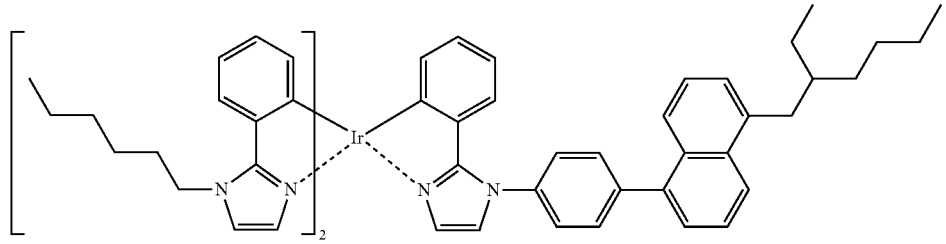
1-39
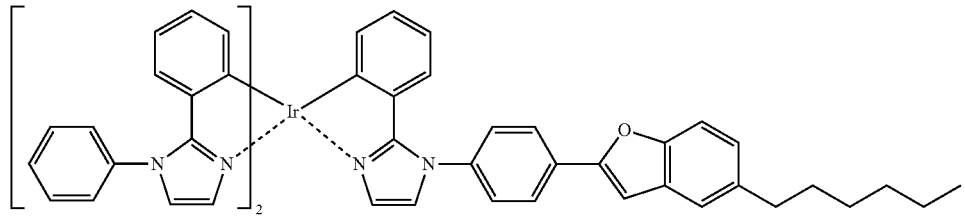
1-40
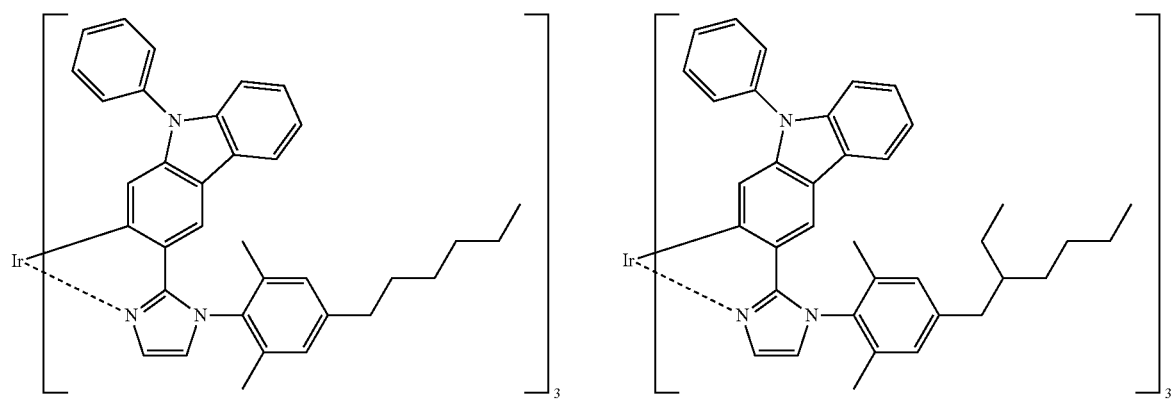
1-41 1-42
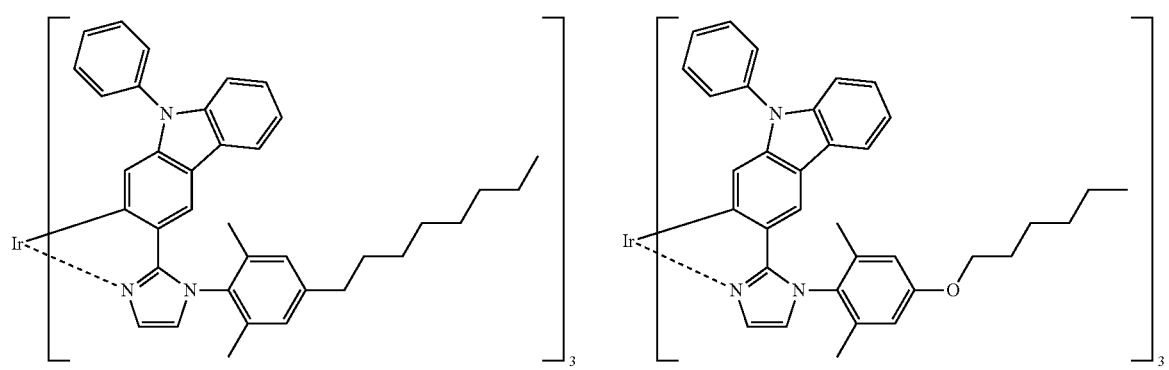
1-43 1-44

-continued
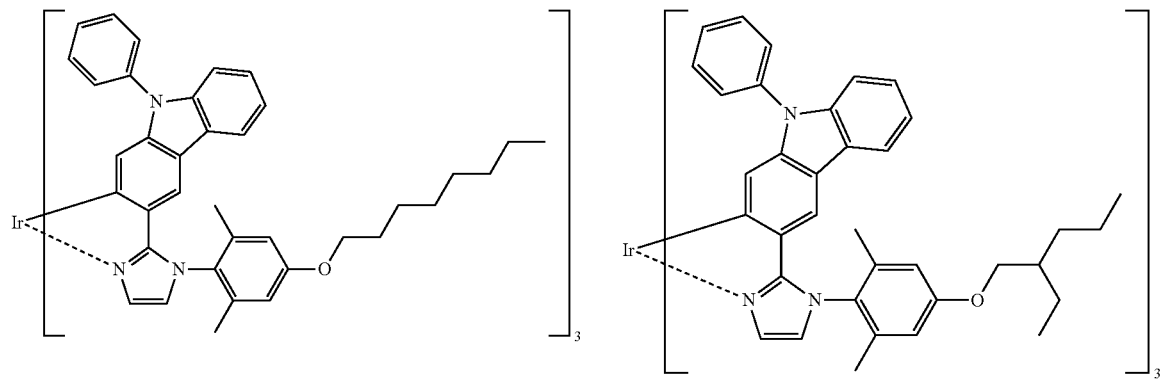
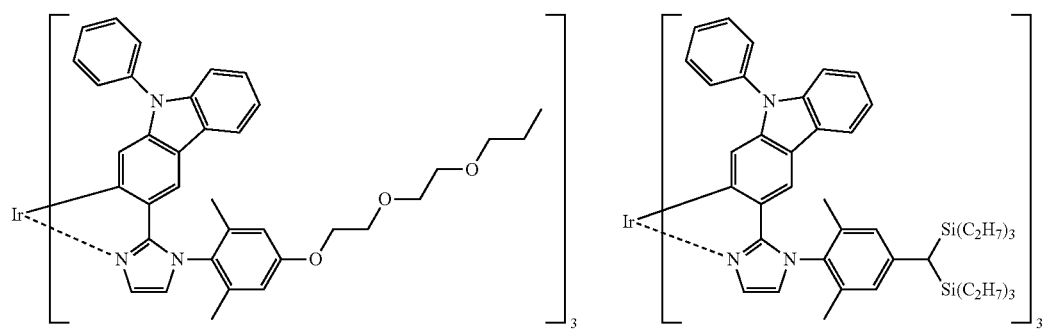
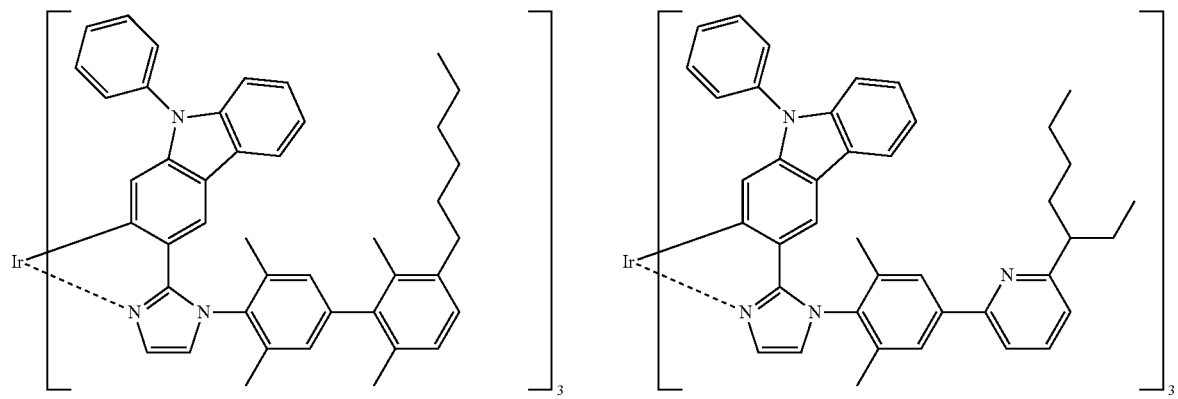
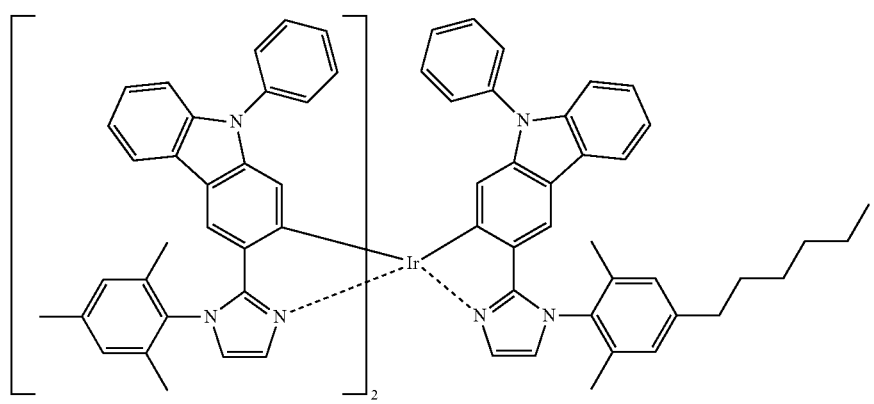

-continued
1-52
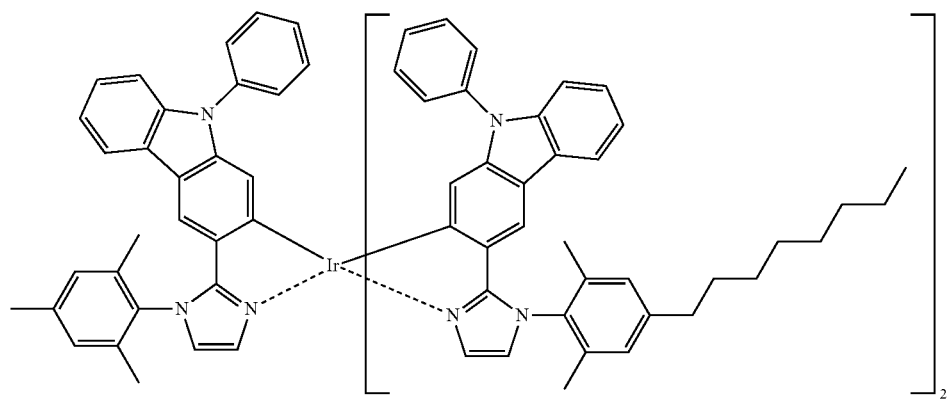
1-53
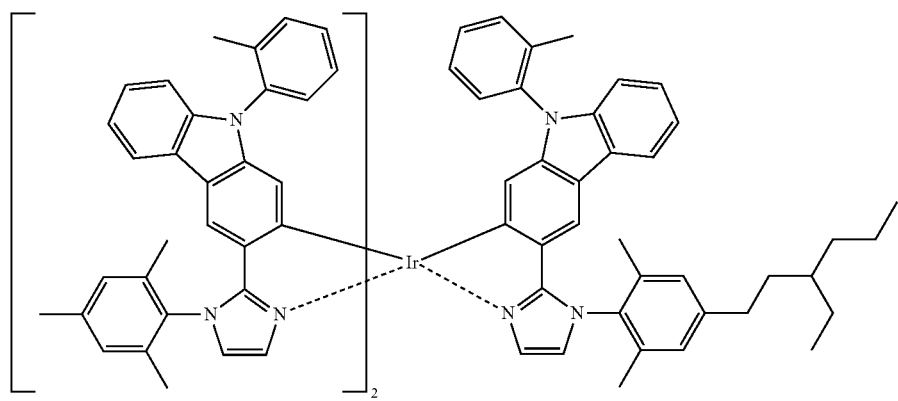
1-54
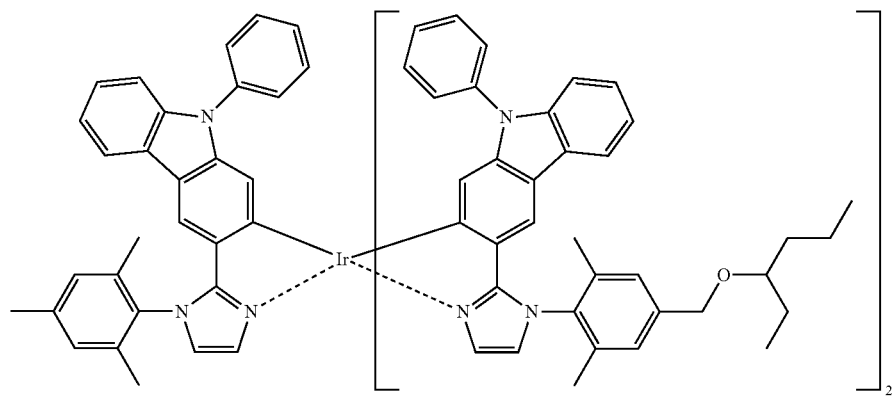
1-55
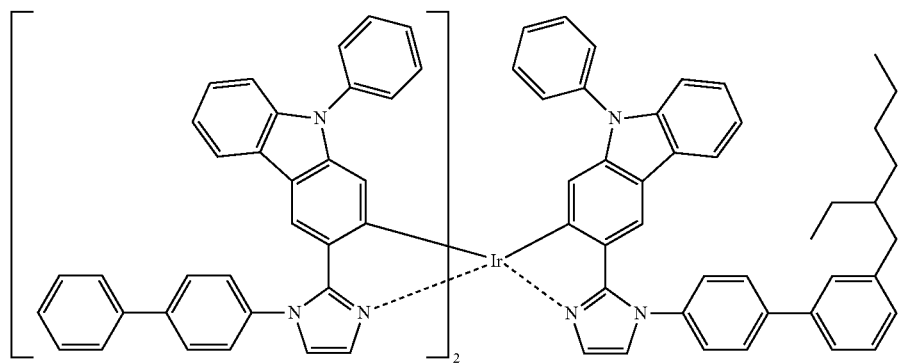

1-56
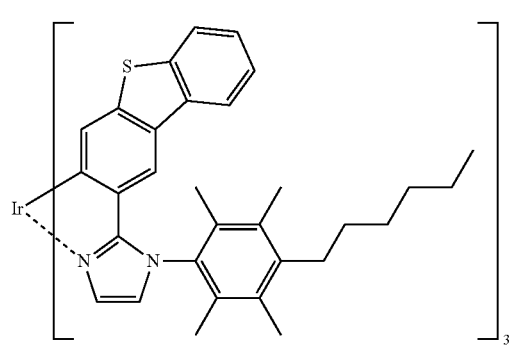
1-57
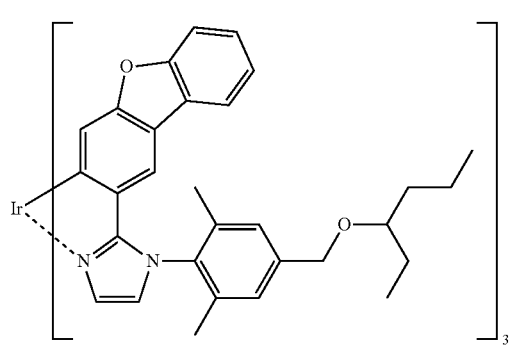
1-58
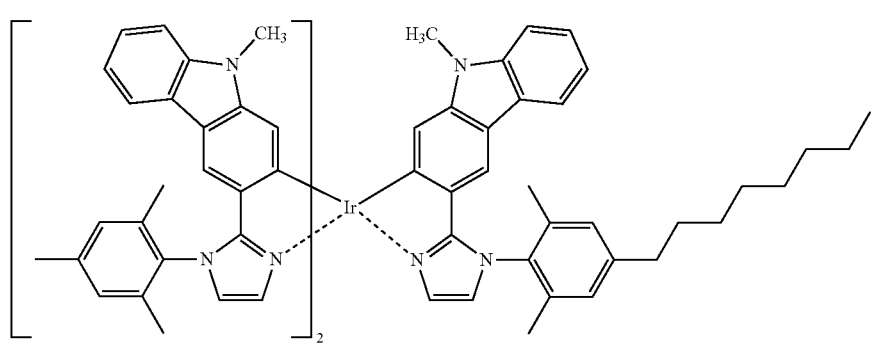
1-59
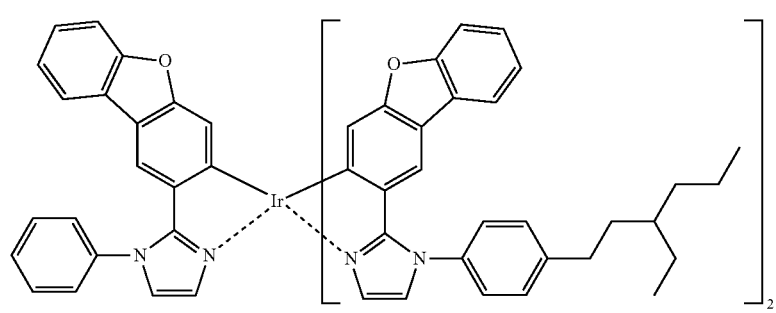
1-60
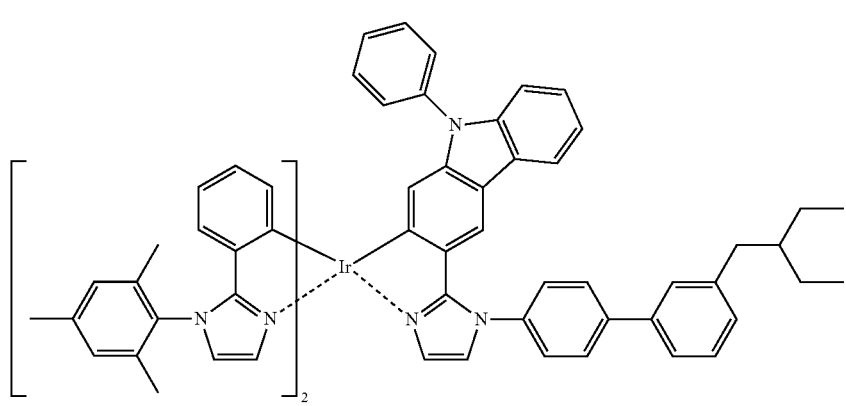

-continued
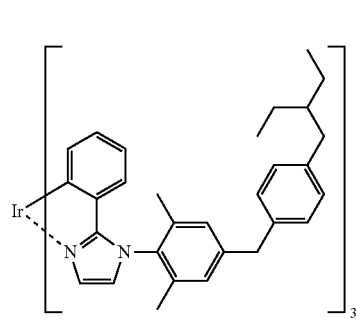
1-61
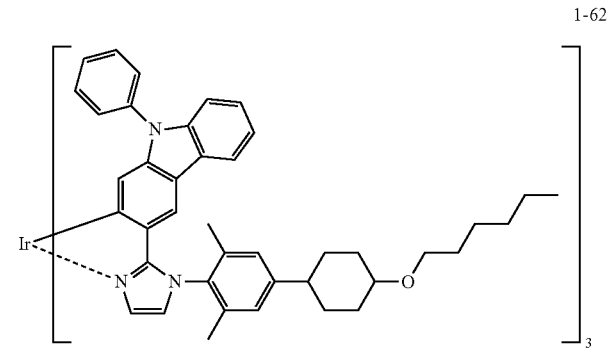
1-62
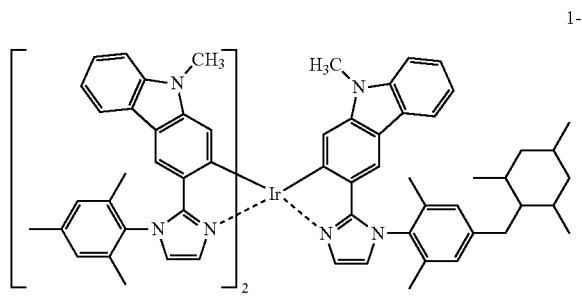
1-63
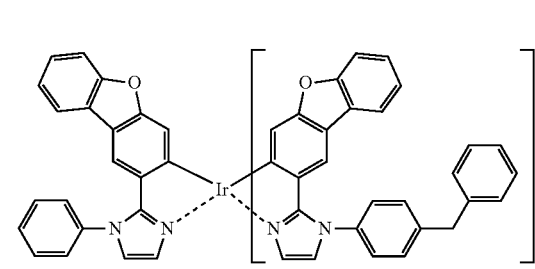
1-64
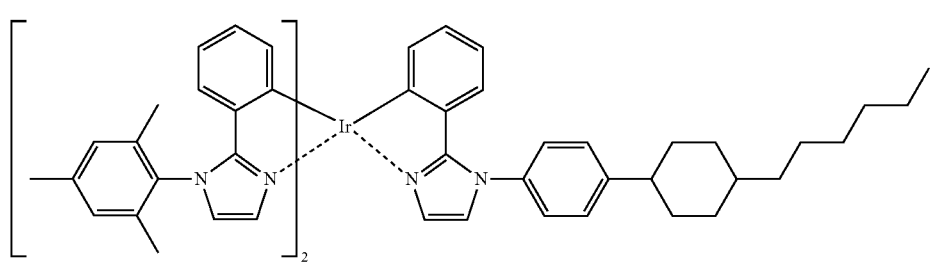
1-65
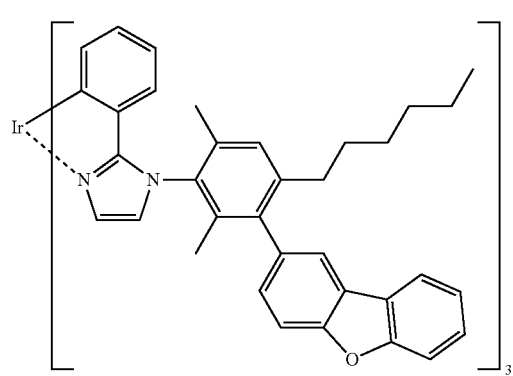
1-66
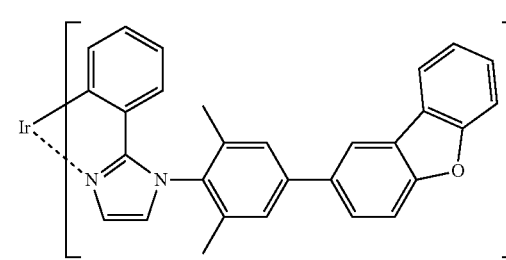
1-67

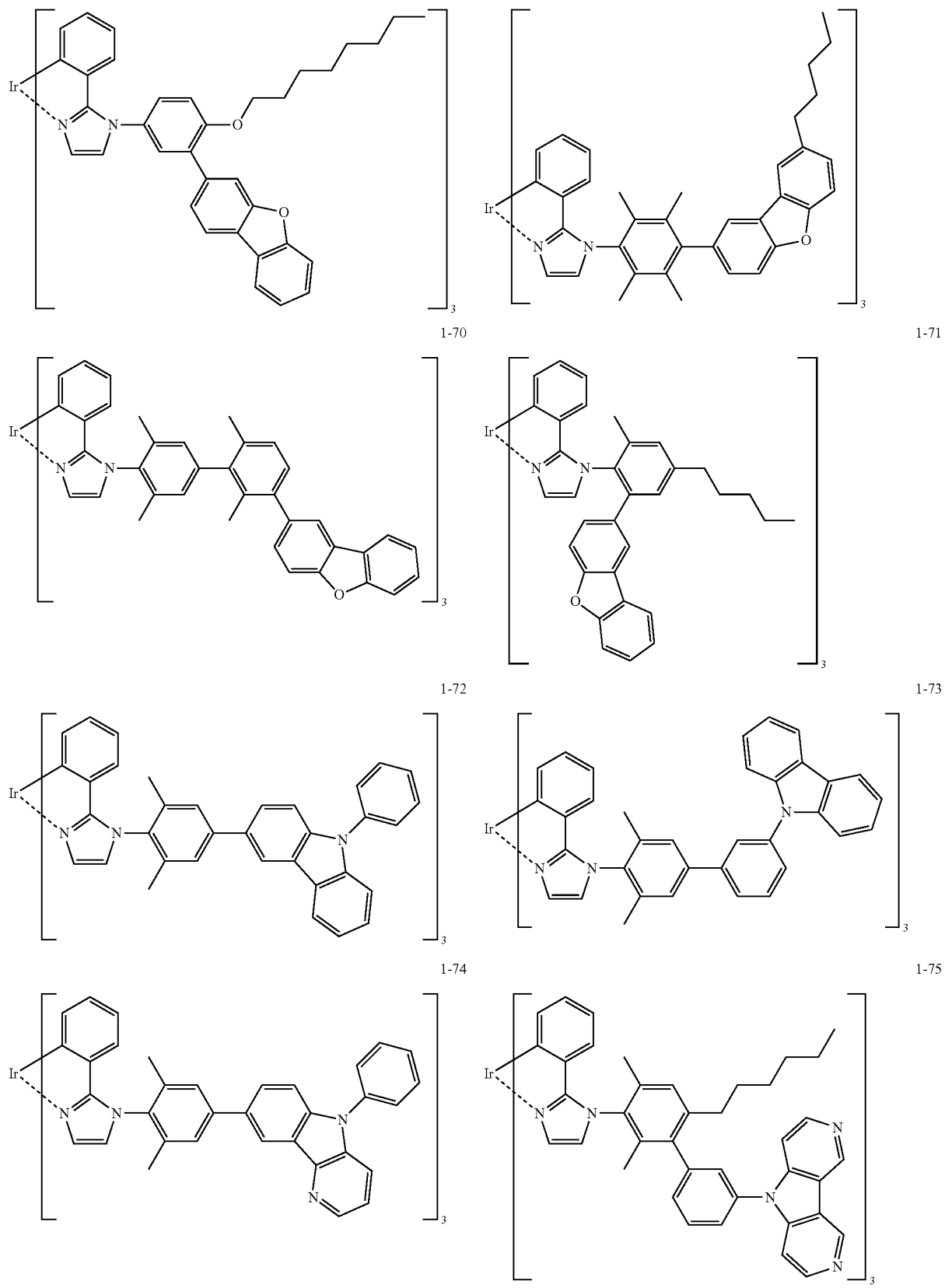

The compounds having a partial structure represented by one of Formulas (1) to (3) of the present invention can be synthesized by applying a method described in such as Organic Letter, vol. 3, No. 16, pp. 2579-2581 (2001), Inorganic Chemistry vol. 30, No. 8, pp. 1685-1687 (1991), J. Am. Chem. Soc., vol. 123, p. 4304 (2001), Inorganic Chemistry vol. 40, No. 7, pp. 1704-1711 (2001), Inorganic Chemistry vol. 41, No. 12, pp. 3055-3066 (2002), New Journal of Chemistry, vol. 26, p. 1171 (2002), Angewandte Chemie International Edition, vol. 38, pp. 1698-1712 (1999), Bulletin of the Chemical Society of Japan, vol. 71, pp. 467-473 (1998), J. Am. Chem. Soc., vol. 125, No. 18, p. 5274-5275 (2003), and J. Am. Chem. Soc., vol. 125, No. 35, p. 10580-10585 (2003), and reference documents described in these documents.

Typical synthesis example of a compound of the present invention is described below for reference.

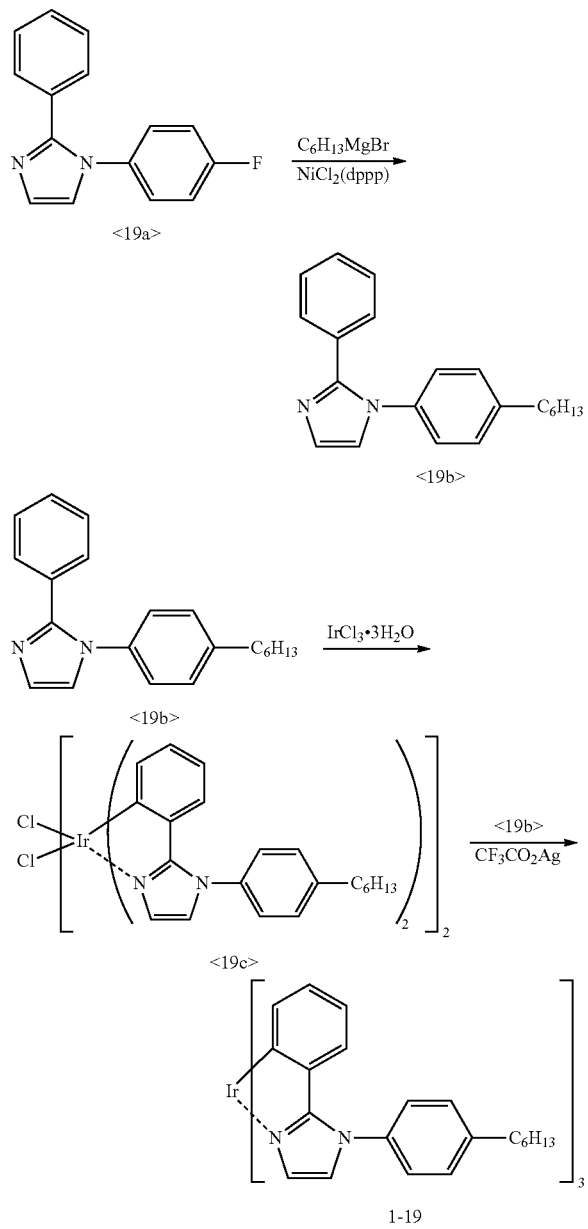

(Synthesis of Compound 1-19)

Synthesis of a Ligand (Compound <19b>)

Into a three-necked 200 ml flask, 5.0 g of Compound <19a> (a compound described in Org. Lett., 2006 (13), 2779-2782) and 0.2 g of [1,3-bis(diphenylphosphino)propane]nickel(II) chloride were charged and the atmosphere in the flask was replaced by nitrogen. And then 100 ml of tetrahydrofuran was added and 11 ml of a 2 moles/L tetrahydrofuran solution of hexylmagnesium chloride was dropped spending 30 minutes. After finishing of the dropping, the system was heated and refluxed for 6 hours and then cooled to a room temperature and the reacting liquid was slowly poured into 500 ml of ice water. The organic layer was separated, washed by a saturated sodium chloride solution and dried by magnesium sulfate. The resultant was concentrated under reduced pressure in a rotary evaporator and the obtained residue was purified by column chromatography. It was confirmed by $^1$H-NMR and Mass-spectrogram that the obtained substance was the objective compound.

Synthesis of Compound 1-19

Into a 100 ml three-necked flask, 0.2 g of Compound <19b> and 0.8 g of iridium(III) chloride trihydrate were charged and the atmosphere in the system was replaced by nitrogen and then 50 ml of 2-ethanolamine and 10 ml of purified water added. The system was heated and stirred at 130° C. for 4 hours, and then 50 ml of methanol was added. Resultant precipitates were separated by filtration and dried to obtain 2.1 g of Compound <19c>.

Into a 100 ml flask, 1.0 g of Compound <19c>, 0.73 g of Compound <19b> and 0.33 g of silver trifluoroacetate were charged and the atmosphere in the flask was replaced by nitrogen. After that, 30 ml of 2-ethoxyethanol was added and the system was heated and stirred at 110° C. for 24 hours. After finishing of reaction, 60 ml of methanol was added. Resultant precipitates were separated by filtration and purified by column chromatography and sublimation to obtain 130 mg of solid substance. It was confirmed by $^1$H-NMR and Mass-spectrogram that the obtained substance was the objective compound.

Specific examples of a preferable layer constitution of an organic electroluminescent element of the present invention are shown below; however, the present invention is not limited thereto.

(i) anode/light emitting layer/electron transport layer/cathode
(ii) anode/positive hole transport layer/light emitting layer/electron transport layer/cathode
(iii) anode/positive hole transport layer/light emitting layer/positive hole inhibition layer/electron transport layer/cathode
(iv) anode/positive hole transport layer/light emitting layer/positive hole inhibition layer/electron transport layer/cathode buffer layer/cathode
(v) anode/anode buffer layer/positive hole transport layer/light emitting layer/positive hole inhibition layer/electron transport layer/cathode buffer layer/cathode In the organic EL element of the present invention, the maximum wavelength of light emitted from the blue light emitting layer is preferably within 430-480 nm, and the green light emitting layer is preferably a monochromatic light emitting layer which results in the maximum wavelength of the emitted light within 510-550 nm, while the red light emitting layer is a monochromatic light emitting layer which results in the maximum wavelength of the emitted light in the range of 600-640 nm. Display devices employing these are preferred. Further, a while light emitting layer is acceptable, which is prepared by laminating at least three of these layers. Further, between the light emitting layers may be present a non-light emitting intermediate layer. As the organic EL element of the present invention, preferred is a white light emitting layer, and illuminating devices employing these are preferred.

Each of the layers which constitute the organic electroluminescent elements of the present invention will now be sequentially detailed.

<<Emitting Layer>>

The emitting layer of the present invention is a layer, which emits light via recombination of electrons and positive holes injected from an electrode or a layer such as an electron transport layer or a positive hole transport layer. The emission portion may be present either within the emitting layer or at the interface between the emitting layer and an adjacent layer thereof.

The total thickness of the light emitting layer is not particularly limited. However, in view of the layer homogeneity, the minimization of application of unnecessary high voltage during light emission, and the stability enhancement of the emitted light color against the drive electric current, the layer thickness is regulated preferably in the range of 2 nm-5 μm, more preferably in the range of 2 nm-200 nm, but most preferably in the range of 10-20 nm.

With regard to preparation of the light emitting layer, light emitting dopants and host compounds, described below, may be subjected to film formation via a conventional thin filming method such as a vacuum deposition method, a spin coating method, a casting method, an LB method, or an ink-jet method.

It is preferable that the light emitting layer of the organic EL element of the present invention incorporates host compounds and at least one kind of light emitting dopants (also referred to as phosphorescence dopants or phosphorescence emitting dopants) and fluorescence dopants.

(Host Compounds (Also Referred to as Light Emitting Hosts)

Host compounds employed in the present invention will now be described.

"Host compounds", as described in the present invention, are defined as compounds, incorporated in a light emitting layer, which result in a weight ratio of at least 20% in the above layer and also result in a phosphorescent quantum yield of the phosphorescence emission of less than 0.1. Further, of compounds incorporated in the light emitting layer, it is preferable that the weight ratio in the aforesaid layer is at least 20%.

An emission host compound of the present invention may be used with plural known host compounds. It is possible to control the transfer of charges by making use of a plurality of host compounds, which results in high efficiency of an organic electroluminescent element. In addition, it is possible to mix a different emission lights by making use of a plurality of emission dopants that will be described later. Any required emission color can be obtained thereby.

Further, an emission host of the present invention may be either a low molecular weight compound or a polymer compound having a repeating unit, in addition to a low molecular weight compound provided with a polymerizing group such as a vinyl group and an epoxy group (an evaporation polymerizing emission host).

A known emission host which may be jointly used is preferably a compound having a positive hole transporting ability and an electron transporting ability, as well as preventing elongation of an emission wavelength and having a high Tg (a glass transition temperature).

As specific examples of an emission host compounds described in the following Documents are preferable.

For example, JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

The following compounds can also be cited.

2-1

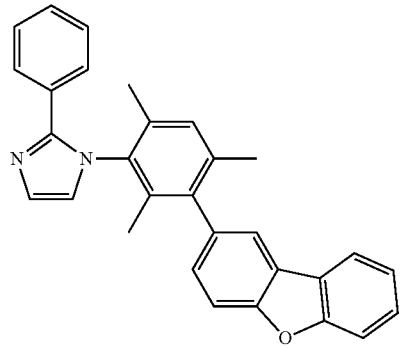

2-2

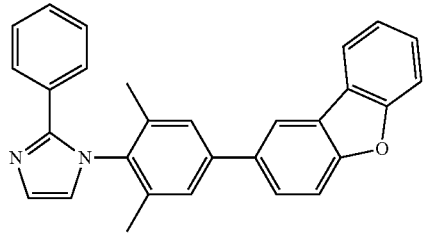

2-3

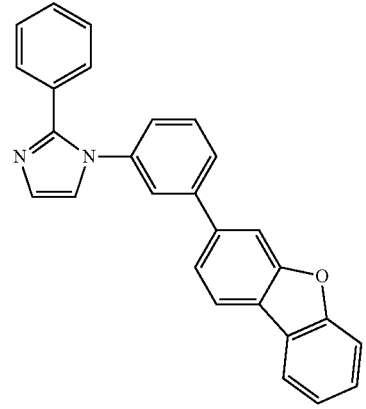

2-4

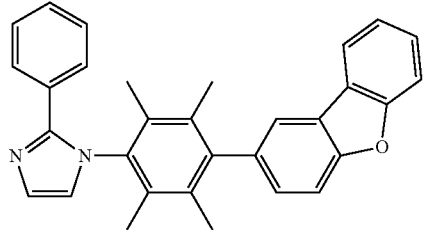

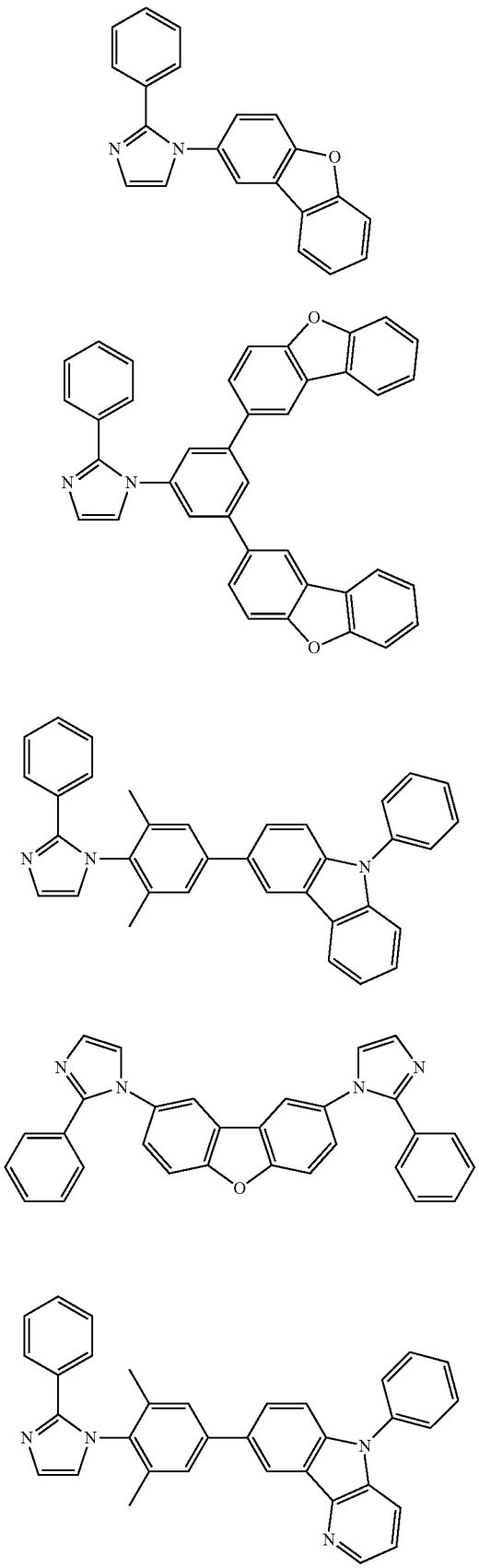

2-5

2-6

2-7

2-8

2-9

2-10

(Emission Dopant)

The emission dopant of the present invention will now be described.

As light emitting dopants according to the present invention, employed may be fluorescent dopants (also referred to as fluorescent compounds), phosphorescence emitting dopants (also referred to as phosphorescent dopants, phosphorescent compounds, phosphorescence emitting compounds, or phosphorescent dopants). However, in view of production of organic EL elements exhibiting higher light emission efficiency, as light emitting dopants (also referred simply to as light emitting materials) employed in the light emitting layer of the organic EL element and light emitting units in the present invention, it is preferable to simultaneously incorporate the aforesaid host compounds and the phosphorescence emitting dopants.

(Phosphorescence-Emitting Dopant)

A phosphorescence emitting dopant of the present invention will be described.

The phosphorescence-emitting dopant of the present invention is a compound, wherein emission from an excited triplet state thereof is observed, specifically, emitting phosphorescence at room temperature (25° C.) and exhibiting a phosphorescence quantum yield of at least 0.01 at 25° C. The phosphorescence quantum yield is preferably at least 0.1.

The phosphorescence quantum yield can be determined via a method described in page 398 of Bunko II of Dai 4 Han Jikken Kagaku Koza 7 (Spectroscopy II of 4th Edition Lecture of Experimental Chemistry 7) (1992, published by Maruzen Co., Ltd.). The phosphorescence quantum yield in a solution can be determined using appropriate solvents. However, it is only necessary for the phosphorescence-emitting dopant of the present invention to exhibit the above phosphorescence quantum yield using any of the appropriate solvents.

Two kinds of principles regarding emission of a phosphorescence-emitting dopant are cited. One is an energy transfer-type, wherein carriers recombine on a host compound on which the carriers are transferred to produce an excited state of the host compound, and then via transfer of this energy to a phosphorescence-emitting dopant, emission from the phosphorescence-emitting dopant is realized. The other is a carrier trap-type, wherein a phosphorescence-emitting dopant serves as a carrier trap and then carriers recombine on the phosphorescence-emitting dopant to generate emission from the phosphorescence-emitting dopant. In each case, the excited state energy of the phosphorescence-emitting dopant is required to be lower than that of the host compound.

Ones selected from known substances usually used in the light emitting layer of organic electroluminescent element can be used for the phosphorescent dopant.

The phosphorescent dopant relating to the present invention is preferably a complex compound containing a metal of Groups 8 to 10 of periodic table and more preferably an iridium compound, an osmium compound, a platinum compound (platinum complex type compound) and a rare metal complex. Among them, the iridium compounds are preferred and the compounds having the partial structure of the present invention represented by Formulas (1), (2) or (3) are most preferable.

It is preferable in the present invention that the following concrete compound is used together with the compound having the partial structure of the present invention represented by Formulas (1), (2) or (3).

Concrete examples of known compound usable as the phosphorescent dopant are shown below but the present invention is not limited to these compounds. These compounds can be synthesized by the method described in Inorg. Chem., 40, 1704-1711.

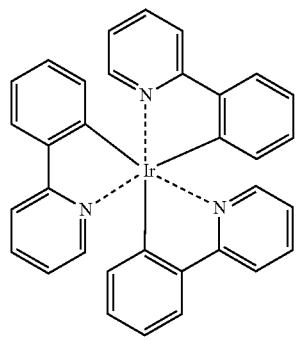

Ir-1

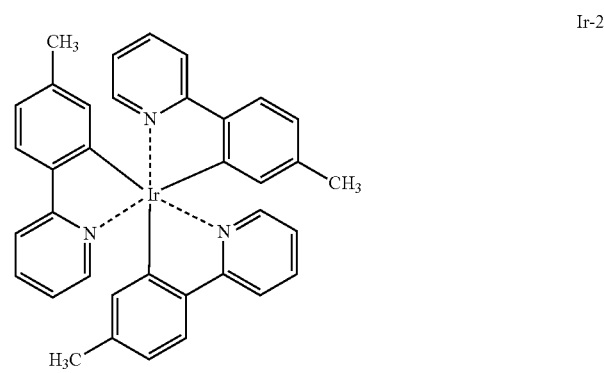

Ir-2

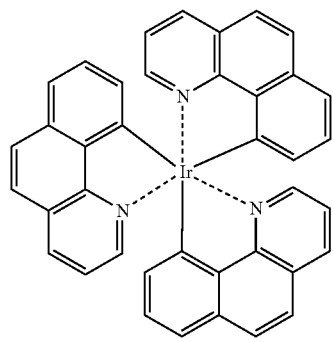

Ir-3

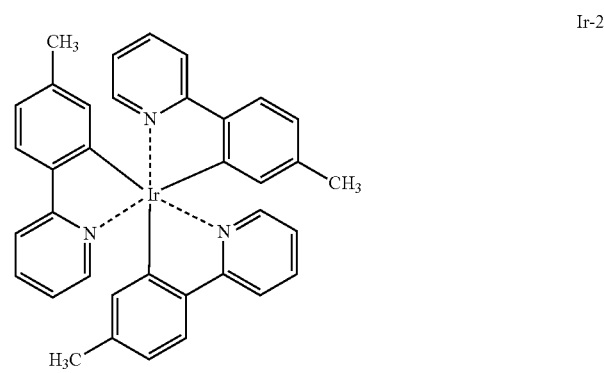

Ir-4

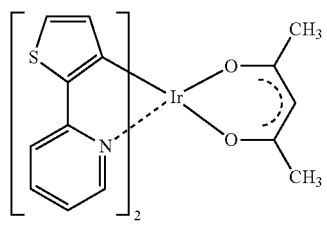

Ir-5

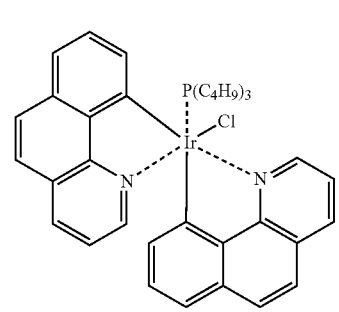

Ir-6

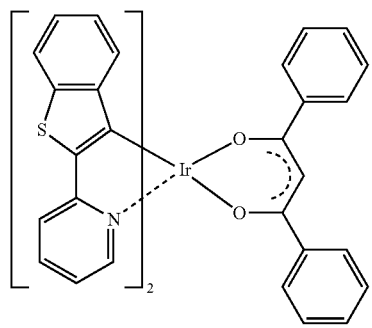

Ir-7

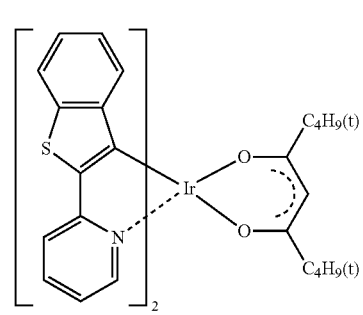

Ir-8

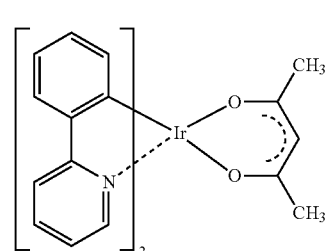

-continued
Ir-9
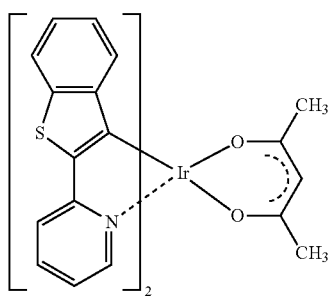
Ir-10
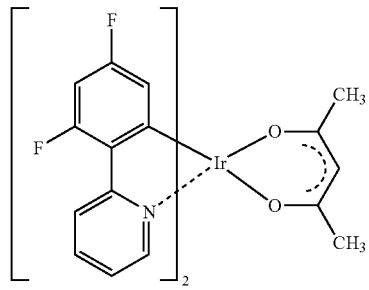
Ir-11
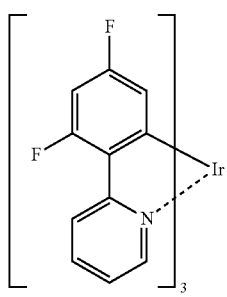
Ir-12
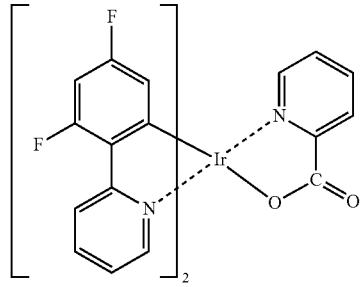
Ir-13
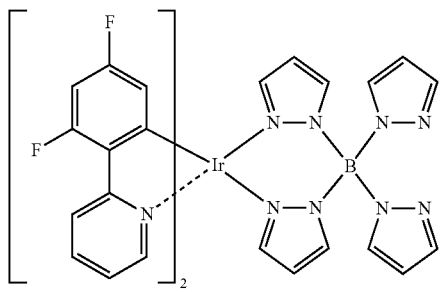
Ir-14
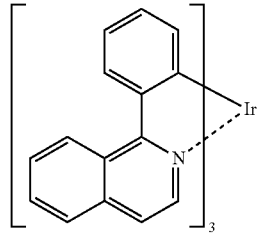
Pt-1
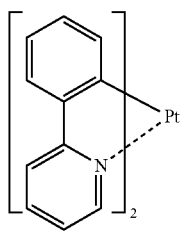
Pt-2
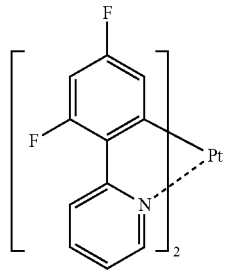
Pt-3
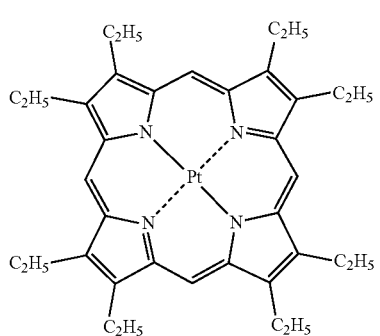

-continued
A-1
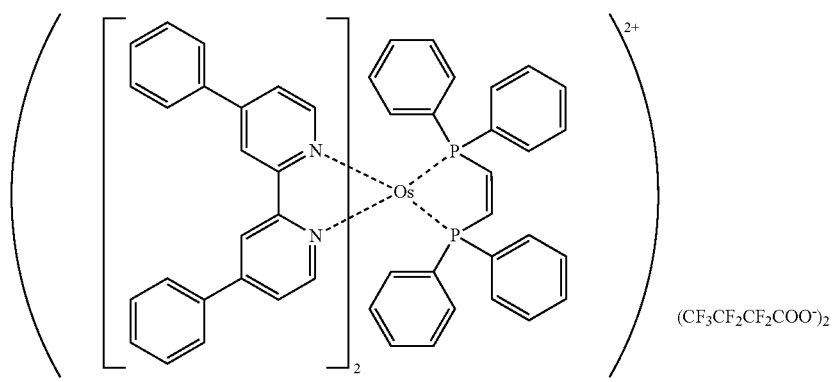
D-1
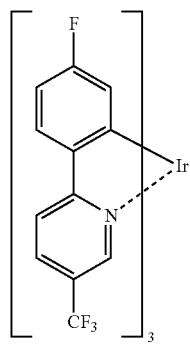
D-2
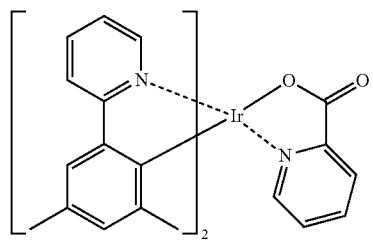
D-3
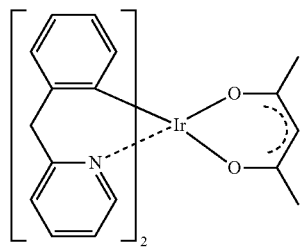
D-4
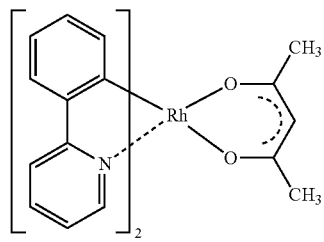
D-5
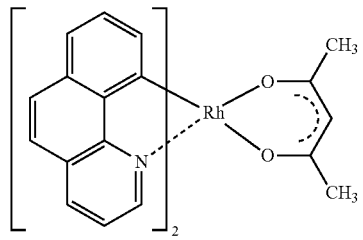
D-6
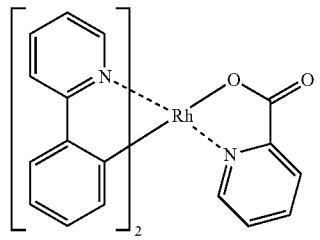
Pd-1
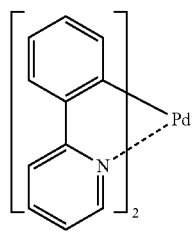
Pd-2
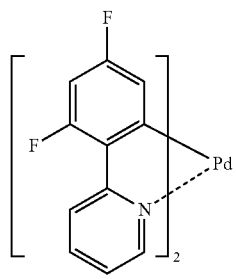

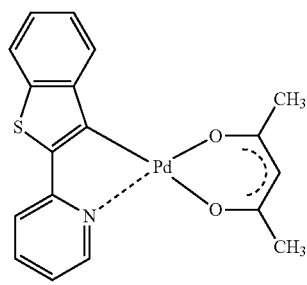

Pd-3

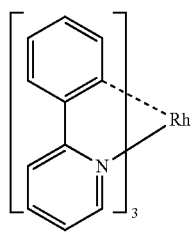

Rh-1

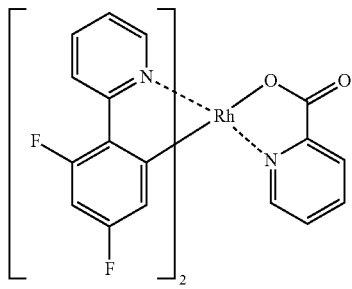

Rh-2

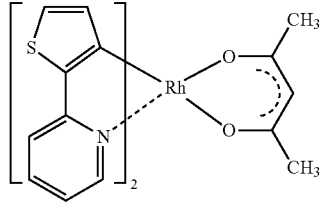

Rh-3

(Fluorescent Dopants (Also Referred to as Fluorescent Compounds))

As fluorescent dopants, listed are coumarin based dyes, pyran based dyes, cyanine based dyes, croconium based dyes, squarylium based dyes, oxobenzanthracene based dyes, fluorescein based dyes, Rhodamine based dyes, pyrylium based dyes, perylene based dyes, stilbene based dyes, polythiophene based dyes, or rare earth complex based fluorescent materials.

An injection layer, an inhibition layer, and an electron transport layer, which are employed as a constituting layer of the organic EL element of the present invention will now be described.

<Injection Layer: Electron Injection Layer, Positive Hole Injection Layer>

An injection layer is appropriately provided and an injection layer includes an electron injection layer and a positive hole injection layer, which may be arranged between an anode and an emitting layer or a positive transfer layer, and between a cathode and an emitting layer or an electron transfer layer, as described above.

An injection layer is a layer which is arranged between an electrode and an organic layer to decrease an operating voltage and to improve an emission luminance, which is detailed in volume 2, chapter 2 (pp. 123-166) of "Organic EL Elements and Industrialization Front thereof (Nov. 30, 1998, published by N. T. S Corp.)", and includes a positive hole injection layer (an anode buffer layer) and an electron injection layer (a cathode buffer layer).

An anode buffer layer (a positive hole injection layer) is also detailed in such as JP-A 9-45479, 9-260062 and 8-288069, and specific examples include such as a phthalocyanine buffer layer comprising such as copper phthalocyanine, an oxide buffer layer comprising such as vanadium oxide, an amorphous carbon buffer layer, and a polymer buffer layer employing conductive polymer such as polythiophene.

A cathode buffer layer (an electron injection layer) is also detailed in such as JP-A 6-325871, 9-17574 and 10-74586, and specific examples include a metal buffer layer comprising such as strontium and aluminum, an alkali metal compound buffer layer comprising such as lithium fluoride, an alkali earth metal compound buffer layer comprising such as magnesium fluoride, and an oxide buffer layer comprising such as aluminum oxide. The above-described buffer layer (injection layer) is preferably a very thin layer, and the layer thickness is preferably in a range of 0.1-100 nm although it depends on a raw material.

<Inhibition Layer: Positive Hole Inhibition Layer, Electron Inhibition Layer>

An inhibition layer is appropriately provided in addition to the basic constitution layers composed of organic thin layers as described above. Examples are described in such as JP-A Nos. 11-204258 and 11-204359 and p. 273 of "Organic Electroluminescent Elements and Industrialization Front Thereof (Nov. 30 (1998), published by N. T. S Corp.)" is applicable to a positive hole inhibition (hole block) layer according to the present invention.

A positive hole inhibition layer, in a broad meaning, is provided with a function of electron transport layer, being composed of a material having a function of transporting an electron but a very small ability of transporting a positive hole, and can improve the recombination probability of an electron and a positive hole. by inhibiting a positive hole while transporting an electron. Further, a constitution of an electron transport layer described later can be appropriately utilized as a positive hole inhibition layer according to the present invention.

The positive hole inhibition layer of the organic EL element of the present invention is preferably arranged adjacent to the light emitting layer.

It is preferable that the positive hole inhibition layer incorporates carbazole derivatives listed as a host compound described above.

Further, in the present intention, in the case in which a plurality of light emitting layers which differ in a plurality of different emitted light colors, it is preferable that the light emitting layer which results in the shortest wavelength of the emitted light maximum wavelength is nearest to the anode in all light emitting layers. However, in such a case, it is preferable to additionally arrange the positive hole inhibition layer between the aforesaid shortest wavelength layer and the light emitting layer secondly near the anode. Further, at least 50% by weight of the compounds incorporated in the positive hole inhibition layer arranged in the aforesaid position preferably exhibits the ionization potential which is greater by at least 0.3 eV than that of the host compounds of the aforesaid shortest wavelength light emitting layer.

The ionization potential is defined as energy which is necessary to release electrons in the HOMO (being the highest occupied molecular orbital) to the vacuum level, and may be determined via, for example, the method described below.

(1) By employing Gaussian98 (Gauaaian98, Revision A. 11. 4, M. J. Frisch, et al. Gaussian 98(Gaussian98, Revision A. 11. 4, M. J. Frisch, et al, Gaussian, Inc., Pittsburgh Pa., 2002), which is a molecular orbital calculation software, produced by Gaussian Co. in the United State of America, and by employing B3LYP/6-31G* as a key word, the value (in terms of corresponding eV unit) was computed, and it is possible to obtain the ionization potential by rouging off the second decimal point. The background, in which the resulting calculated values are effective, is that the calculated values obtained by the above method exhibit high relationship with the experimental values.

(2) It is possible to determine the ionization potential via a method in which ionization potential is directly determined employing a photoelectron spectrometry. For example, by employing a low energy electron spectrophotometer "Model AC-1", produced by Riken Keiki Co., or appropriately employ a method known as an ultraviolet light electron spectrometry.

On the other hand, the electron inhibition layer, as described herein, has a function of the positive hole transport layer in a broad sense, and is composed of materials having markedly small capability of electron transport, while having capability of transporting positive holes and enables to enhance the recombination probability of electrons and positive holes by inhibiting electrons, while transporting electrons. Further, it is possible to employ the constitution of the positive hole transport layer, described below, as an electron inhibition layer when needed. The thickness of the positive hole inhibition layer and the electron transport layer according to the present invention is preferably 3-100 nm, but is more preferably 5-30 nm.

<Positive Hole Transport Layer>

A positive hole transport layer contains a material having a function of transporting a positive hole, and in a broad meaning, a positive hole injection layer and an electron inhibition layer are also included in a positive hole transport layer. A single layer of or plural layers of a positive hole transport layer may be provided.

A positive hole transport material is those having any one of a property to inject or transport a positive hole or a barrier property to an electron, and may be either an organic substance or an inorganic substance. For example, listed are a triazole derivative, an oxadiazole derivative, an imidazole derivative, a polyarylalkane derivative, a pyrazolone derivative, a phenylenediamine derivative, an arylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive polymer oligomer and specifically preferably such as thiophene oligomer.

As a positive hole transport material, those described above can be utilized, however, it is preferable to utilized a porphyrin compound, an aromatic tertiary amine compound and a styrylamine compound, and specifically preferably an aromatic tertiary amine compound.

Typical examples of an aromatic tertiary amine compound and a styrylamine compound include N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl 4,4'-diaminobiphenyl; 1,1-bis(4-di-p-tolylaminophenyl)-4-phenylcyclohexane; bis(4-dimethylamino-2-methyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminophenylether; 4,4'-bis(diphenylamino)quadriphenyl; N,N,N-tri(p-tolyl)amine; 4-(di-p-tolylamino)-4'-[4-(di-p-triamino)styryl]stilbene; 4-N,N-diphenylamino-(2-diphenylvinyl)benzene; 3-methoxy-4'-N,N-diphenylaminostilbene; and N-phenylcarbazole, in addition to those having two condensed aromatic rings in a molecule described in U.S. Pat. No. 5,061,569, such as 4,4'-bis[N-(1-naphthyl)-N-phenylamino]biphenyl (NDP), and 4,4',4"-tris[N-(3-methylphenyl)-N-phenylamino]triphenylamine (MDTDATA), in which three of triphenylamine units are bonded in a star burst form, described in JP-A 4-308688.

Polymer materials, in which these materials are introduced in a polymer chain or constitute the main chain of polymer, can be also utilized. Further, an inorganic compound such as a p type-Si and a p type-SiC can be utilized as a positive hole injection material and a positive hole transport material Further, it is possible to employ so-called p type positive hole transport materials, as described in Japanese Patent Publication Open to Public Inspection (hereinafter referred to as JP-A) No. 11-251067, and J. Huang et al. reference (Applied Physics Letters 80 (2002), p. 139). In the present invention, since high efficiency light emitting elements are prepared, it is preferable to employ these materials.

The positive hole transport layer can be prepared by forming a thin layer made of the above-described positive hole transport material according to a method well known in the art such as a vacuum evaporation method, a spin coating method, a cast method, an inkjet method and a LB method. The layer thickness of a positive hole transport layer is not specifically limited, however, it is generally 5 nm-5 μm, and preferably 5 nm-200 nm. This positive transport layer may have a single layer structure composed of one or not less than two types of the above described materials.

Further, it is possible to employ a positive hole transport layer of a higher p property which is doped with impurities. As its example, listed are those described in each of JP-A Nos. 4-297076, 2000-196140, 2001-102175, as well as in J. Appl. Phys., 95, 5773 (2004).

In the present invention, it is preferable to employ a positive hole transport layer of such a high p property, since it is possible to produce an element of lower electric power consumption.

<Electron Transport Layer>

An electron transfer layer is composed of a material having a function to transfer an electron, and an electron injection layer and a positive hole inhibition layer are included in an electron transfer layer in a broad meaning. A single layer or plural layers of an electron transfer layer may be provided.

Heretofore, when an electron transport layer is composed of single layer and a plurality of layers, electron transport materials (also functioning as a positive hole inhibition material) employed in the electron transport layer adjacent to the cathode side with respect to the light emitting layer, electrons ejected from the cathode may be transported to the light emitting layer. As such materials, any of the conventional compounds may be selected and employed. Examples of these compounds include such as a nitro-substituted fluorene derivative, a diphenylquinone derivative, a thiopyradineoxide derivative, carbodiimide, a fluorenylidenemethane derivative, anthraquinonedimethane, an anthraquinone derivative, an anthrone derivative and an oxadiazole derivative. Further, a thiazole derivative in which an oxygen atom in the oxadiazole ring of the above-described oxadiazole derivative is substituted by a sulfur atom, and a quinoxaline derivative having a quinoxaline ring which is known as an electron attracting group can be utilized as an electron transfer material. Polymer materials, in which these materials are introduced in a polymer chain or these materials form the main chain of polymer, can be also utilized.

Further, a metal complex of a 8-quinolinol derivative such as tris(8-quinolinol)aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol) zinc (Znq); and metal complexes in which a central metal of the aforesaid metal complexes is substituted by In, Mg, Cu, Ca, Sn, Ga or Pb, can be also utilized as an electron transfer material.

Further, metal-free or metal phthalocyanine, or those the terminal of which is substituted by an alkyl group and a sulfonic acid group, can be preferably utilized as an electron transfer material. Further, distyrylpyrazine derivative, which has been exemplified as a material of an emitting layer, can be also utilized as an electron transfer material, and, similarly to the case of a positive hole injection layer and a positive hole transfer layer, an inorganic semiconductor such as an n-type-Si and an n-type-SiC can be also utilized as an electron transfer material.

This electron transport layer can be prepared by forming a thin layer made of the above-described electron transport material according to a method well known in the art such as a vacuum evaporation method, a spin coating method, a cast method, an inkjet method and a LB method. The layer thickness of an electron transport layer is not specifically limited; however, it is generally 5 nm-5 μm, and preferably 5 nm-200 nm. This electron transport layer may have a single layer structure composed of one or not less than two types of the above described materials.

Further, it is possible to employ an electron transport layer doped with impurities, which exhibits high n property. Examples thereof include those, described in JP-A Nos. 4-297076, 10-270172, 2000-196140, 2001-102175, as well as J. Appl. Phys., 95, 5773 (2004).

The present invention is preferable since by employing an electron transport layer of such a high n property electron transport layer, it is possible to preparer an element of further lowered electric power consumption.

<Anode>

As an anode according to an organic electroluminescent element of the present invention, those comprising metal, alloy, a conductive compound, which is provided with a large work function (not less than 4 eV), and a mixture thereof as an electrode substance are preferably utilized. Specific examples of such an electrode substance include a conductive transparent material such as metal like Au, CuI, indium tin oxide (ITO), $SnO_2$ and ZnO. Further, a material such as IDIXO ($In_2O_3$—ZnO), which can prepare an amorphous and transparent electrode, may be also utilized. As for an anode, these electrode substances may be made into a thin layer by a method such as evaporation or spattering and a pattern of a desired form may be formed by means of photolithography, or in the case of requirement of pattern precision is not so severe (not less than 100 μm), a pattern may be formed through a mask of a desired form at the time of evaporation or spattering of the above-described substance.

Alternatively, when coatable materials such as organic electrically conductive compounds are employed, it is possible to employ a wet system filming method such as a printing system or a coating system. When emission is taken out of this anode, the transmittance is preferably set to not less than 10% and the sheet resistance as an anode is preferably not more than a few hundreds Ω/□. Further, although the layer thickness depends on a material, it is generally selected in a range of 10-1,000 nm and preferably of 10-200 nm.

<Cathode>

On the other hand, as a cathode according to the present invention, metal, alloy, a conductive compound and a mixture thereof, which have a small work function (not more than 4 eV), are utilized as an electrode substance. Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal.

Among them, with respect to an electron injection property and durability against such as oxidation, preferable are a mixture of electron injecting metal with the second metal which is stable metal having a work function larger than electron injecting metal, such as a magnesium/silver mixture, a magnesium/aluminum mixture, a magnesium/indium mixture, an aluminum/aluminum oxide ($Al_2O_3$) mixture and a lithium/aluminum mixture, and aluminum. As for a cathode, these electrode substances may be made into a thin layer by a method such as evaporation or spattering.

Further, the sheet resistance as a cathode is preferably not more than a few hundreds Ω/□ and the layer thickness is generally selected in a range of 10-1,000 nm and preferably of 10-200 nm.

Herein, to transmit emission, either one of an anode or a cathode of an organic electroluminescent element is preferably transparent or translucent to improve the mission luminance.

Further, after forming, on the cathode, the above metals at a film thickness of 1-20 nm, it is possible to prepare a transparent or translucent cathode in such a manner that electrically conductive transparent materials are prepared thereon. By applying the above, it is possible to produce an element in which both anode and cathode are transparent.

<Substrate>

A substrate according to an organic electroluminescent element of the present invention is not specifically limited to a specific type of substrate such as glass and plastics. They may be transparent or opaque.

However, a transparent substrate is preferable when the emitting light is taken from the side of substrate. Substrates preferably utilized includes such as glass, quartz and transparent resin film. A specifically preferable substrate is resin film capable of providing an organic electroluminescent element with a flexible property.

Resin film includes such as: polyesters such as polyethylene terephthalate (PET) and polyethylene naphthalate (PEN); polyethylene, polypropyrene; cellulose esters or their derivatives such as cellophane, cellulose diacetate, cellulose triacetate, cellulose acetate butylate, cellulose acetate propionate (CAP), cellulose acetate phthalate (TAC) and cellulose nitrate; polyvinylidene chloride, polyvinyl alcohol, polyethylene vinyl alcohol, syndiotactic polystyrene, polycarbonate, norbornene resin, polymethylpentene, polyether ketone, polyimide, polyether sulfone (PES), polyphenylene sulfide, polysulfones, polyetherimide, polyether ketone imide, polyamide, fluororesin, Nylon, polymethylmethacrylate, acrylic resin, polyacrylate; and cycloolefine resins such as ARTON (produced by JSR Co. Ltd.) and APEL (produce by Mitsui Chemicals, Inc.)

On the surface of a resin film, formed may be a film incorporating inorganic and organic compounds or a hybrid film of both. Barrier films are preferred at a water vapor permeability ($25\pm0.5°$ C., and relative humidity ($90\pm2$) % RH) of at most 0.01 g/($m^2 \cdot 24$ h), determined based on JIS K 7129-1992. Further, high barrier films are preferred at an oxygen permeability of at most $1\times10^{-3}$ ml/($m^2 \cdot 24$ h·MPa), and at a water vapor permeability of at most $10^{-5}$ g/($m^2 \cdot 24$ h), determined based on JIS K 7126-1987.

As materials forming a barrier film, employed may be those which retard penetration of moisture and oxygen, which deteriorate the element. For example, it is possible to employ silicon oxide, silicon dioxide, and silicon nitride. Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited, and examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method, a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel, films, opaque resin substrates, and ceramic substrates.

The external extraction efficiency of light emitted by the organic EL element of the present invention is preferably at least 1% at room temperature, but is more preferably at least 5%. External extraction quantum yield (%)=the number of photons emitted by the organic EL element to the exterior/the number of electrons fed to organic EL element Further, even by simultaneously employing color hue improving filters such as a color filter, simultaneously employed may be color conversion filters which convert emitted light color from the organic EL element to multicolor by employing fluorescent materials. When the color conversion filters are employed, it is preferable that λmax of light emitted by the organic EL element is at least 480 nm.

<<Sealing>>

As sealing means employed in the present invention, listed may be, for example, a method in which sealing members, electrodes, and a supporting substrate are subjected to adhesion via adhesives.

The sealing members may be arranged to cover the display region of an organic EL element, and may be an engraved plate or a flat plate. Neither transparency nor electrical insulation is limited.

Specifically listed are glass plates, polymer plate-films, metal plates, and films. Specifically, it is possible to list, as glass plates, soda-lime glass, barium-strontium containing glass, lead glass, aluminosilicate glass, borosilicate glass, bariumborosilicate glass, and quartz. Further, listed as polymer plates may be polycarbonate, acryl, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to convert the element to a thin film, it is possible to preferably employ a metal film. Further, the oxygen permeability of the polymer film is preferably at most $1\times10^{-3}$ ml/($m^2 \cdot 24$ h·MPa), determined by the method based on JIS K 7126-1987, while its water vapor permeability (at $25\pm0.5°$ C. and relative humidity ($90\pm2$) %) is at most $10^{-5}$ g/($m^2 \cdot 24$ h), determined by the method based on JIS K 7129-1992.

Conversion of the sealing member into concave is carried out employing a sand blast process or a chemical etching process.

In practice, as adhesives, listed may be photo-curing and heat-curing types having a reactive vinyl group of acrylic acid based oligomers and methacrylic acid, as well as moisture curing types such as 2-cyanoacrylates. Further listed may be thermal and chemical curing types (mixtures of two liquids) such as epoxy based ones. Still further listed may be hot-melt type polyamides, polyesters, and polyolefins. Yet further listed may be cationically curable type ultraviolet radiation curable type epoxy resin adhesives.

In addition, since an organic EL element is occasionally deteriorated via a thermal process, those are preferred which enable adhesion and curing between room temperature and 80° C. Further, desiccating agents may be dispersed into the aforesaid adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials forming the aforesaid film may be those which exhibit functions to retard penetration of those such as moisture or oxygen which results in deterioration. For example, it is possible to employ silicon oxide, silicon dioxide, and silicon nitride. Still further, in order to improve brittleness of the aforesaid film, it is preferable that a laminated layer structure is formed, which is composed of these inorganic layers and layers composed of organic materials. Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

In a gas phase and a liquid phase, it is preferable to inject inert gases such as nitrogen or argon, and inactive liquids such as fluorinated hydrocarbon or silicone oil into the space between the sealing member and the surface region of the organic EL element. Further, it is possible to form vacuum. Still further, it is possible to enclose hygroscopic compounds in the interior.

Examples of hygroscopic compounds include metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides.

<<Protective Film and Protective Plate>>

The aforesaid sealing film on the side which nips the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, whereby it is preferable to arrange the protective film or the protective plate described above. Usable materials for these include glass plates, polymer plate-films, and metal plate-films which are similar to those employed for the aforesaid sealing. However, in terms of light weight and a decrease in thickness, it is preferable to employ polymer films.

<<Light Extraction>>

It is generally known that an organic EL element emits light in the interior of the layer exhibiting the refractive index (being about 1.7-about 2.1) which is greater than that of air, whereby only about 15-about 20% of light generated in the light emitting layer is extracted. This is due to the fact that light incident to an interface (being an interface of a transparent substrate to air) at an angle of θ which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction of the element side surface.

Means to enhance the efficiency of the aforesaid light extraction include, for example, a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the light emitting body (JP-A No. 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between the substrate and any of the layers such as the transparent electrode layer or the light emitting layer (including between the substrate and the outside).

By combining these means, the present invention enables the production of elements which exhibit higher luminance or excel in durability.

When a low refractive index medium of a thickness, which is greater than the wavelength of light, is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5-about 1.7, the refractive index of the low refractive index layer is preferably at most approximately 1.5, but is more preferably at most 1.35.

Further, thickness of the low refractive index medium is preferably at least two times the wavelength in the medium. The reason is that when the thickness of the low refractive index medium reaches nearly the wavelength of light so that electromagnetic waves oozed via evernescent enter into the substrate, effects of the low refractive index layer are lowered.

The method in which the interface which results in total reflection or a diffraction grating is introduced in any of the media is characterized in that light extraction efficiency is significantly enhanced. The above method works as follows. By utilizing properties of the diffraction grating capable of changing the light direction to the specific direction different from diffraction via so-called Bragg diffraction such as primary diffraction or secondary diffraction of the diffraction grating, of light emitted from the light emitting layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive index. The reason is as follows. Since light emitted in the light emitting layer is randomly generated to all directions, in a common one-dimensional diffraction grating exhibiting a periodic refractive index distribution only in a certain direction, light which travels to the specific direction is only diffracted, whereby light extraction efficiency is not sufficiently enhanced. However, by changing the refractive index distribution to a two-dimensional one, light, which travels to all directions, is diffracted, whereby the light extraction efficiency is enhanced.

As noted above, a position to introduce a diffraction grating may be between any layers or in a medium (in a transparent substrate or a transparent electrode). However, a position near the organic light emitting layer, where light is generated, is desirous.

In this case, the cycle of the diffraction grating is preferably about ½-about 3 times the wavelength of light in the medium.

The preferable arrangement of the diffraction grating is such that the arrangement is two-dimensionally repeated in the form of a square lattice, a triangular lattice, or a honeycomb lattice.

<<Light Collection Sheet>>

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 μm and an apex angle of 90 degrees are two-dimensionally arranged on the light extraction side of the substrate. The side length is preferably 10-100 μm. When it is less than the lower limit, coloration results due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited. As shapes of a prism sheet employed may be, for example, Δ shaped stripes of an apex angle of 90 degrees and a pitch of 50 μm formed on a base material, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

<<Preparation Method of Organic EL Element>>

As one example of the preparation method of the organic EL element of the present invention, the preparation method of the organic EL element composed of anode/positive hole injection layer/positive hole transport layer/light emitting layer/electron transport layer/electron injection layer/cathode will be described.

Initially, a thin film composed of desired electrode substances, for example, anode substances is formed on an appropriate base material to reach a thickness of at most 1 μm but preferably 10-200 nm, employing a method such as vapor deposition or sputtering, whereby an anode is prepared.

Subsequently, on the above, formed are organic compound thin layers including a positive hole injection layer, a positive hole transport layer, a light emitting layer, a positive hole inhibition layer, an electron transport layer, and an electron injection layer, which are organic EL element materials.

Methods to form each of these layers include, as described above, a vapor deposition method and a wet process (a spin coating method, a casting method, an ink-jet method, and a printing method). In the present invention, in view of easy formation of a homogeneous film and rare formation of pin holes, preferred is film formation via the coating method such as the spin coating method, the ink-jet method, or the printing method.

As liquid media which are employed to dissolve or disperse organic metal complexes according to the present invention, employed may be, for example, ketones such as methyl ethyl ketone or cyclohexanone; fatty acid esters such as ethyl acetate; halogenated hydrocarbons such as dichlorobenzene; aromatic hydrocarbons such as toluene, xylene, mesitylene and cyclohexylbenzene; aliphatic hydrocarbons such as cyclohexane, decaline and dodecane; and organic solvents such as DMF or DMSO. Further, with regard to dispersion methods, it is possible to achieve dispersion employing dispersion methods such as ultrasonic waves, high shearing force dispersion or media dispersion.

After forming these layers, a thin layer composed of cathode materials is formed on the above layers via a method such as vapor deposition or sputtering so that the film thickness reaches at most 1 μm, but is preferably in the range of 50-200 nm, whereby a cathode is arranged, and the desired organic EL element is prepared.

Further, by reversing the preparation order, it is possible to achieve preparation in order of a cathode, an electron injection layer, an electron transport layer, a light emitting layer, a positive hole transport layer, a positive hole injection layer, and an anode. When direct current voltage is applied to the multicolor display device prepared as above, the anode is employed as +polarity, while the cathode is employed as −polarity. When 2-40 V is applied, it is possible to observe light emission. Further, alternating current voltage may be applied. The wave form of applied alternating current voltage is not specified.

<<Application>>

It is possible to employ the organic EL element of the present invention as display devices, displays, and various types of light emitting sources. Examples of light emitting sources include, but are not limited to lighting apparatuses (home lighting and car lighting), clocks, backlights for liquid crystals, sign advertisements, signals, light sources of light memory media, light sources of electrophotographic copiers, light sources of light communication processors, and light sources of light sensors.

If needed, the organic EL element of the present invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

Figure 4:
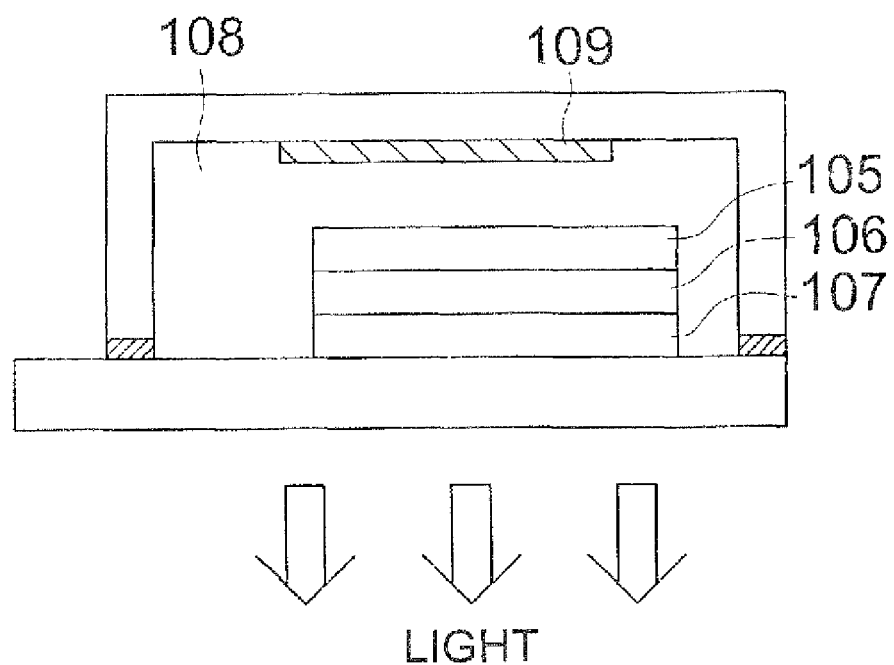
FIG. 4 is a schematic cross-sectional view of a lighting device.

Color of light emitted by the organic EL element of the present invention and compounds according to the present invention is specified as follows. In FIG. 4.16 on page 108 of "Shinpen Shikisai Kagaku Handbook (New Edition Color Science Handbook)" (edited by The Color Science Association of Japan, Tokyo Daigaku Shuppan Kai, 1985), values determined via a spectroradiometric luminance meter CS-1000 (produced by Konica Minolta Sensing Inc.) are applied to the CIE chromaticity coordinate, whereby the color is specified.

Further, when the organic EL element of the present invention is a white element, "white", as described herein, means that when 2-degree viewing angle front luminance is determined via the aforesaid method, chromaticity in the CIE 1931 Color Specification System is within the region of X=0.33±0.07 and Y=0.33±0.07.

EXAMPLES

The present invention is described below referring examples but the present invention is not limited to them.

Example 1

Preparation of Organic Electroluminescent Element 1

A glass substrate of 100 mm×100 mm×1.1 mm on which an ITO (indium tin oxide) layer of 100 nm was provided as an anode (NA-45 manufactured by NH Techno Glass Corp.) was subjected to patterning and thus obtained transparent substrate plate having the ITO transparent anode was washed by ultrasonic treatment using isopropyl alcohol, dried by dried nitrogen gas and subjected to UV-ozone cleaning for 5 minutes.

On the transparent substrate plate, a solution prepared by diluting poly(3,4-ethylenedioxythiophene)-polystyrene-sulfonate (PEDOT/PSS, Baytron P Al 4083 manufactured by Bayer) with purified water by 70 weight percent was coated by spin coating at 3,000 rpm for 30 seconds and dried under vacuum for 1 hour at 200° C. to provide a first positive hole transfer layer.

On the first positive hole transfer layer, a solution prepared by dissolving 30 mg of m-CP and 1.5 mg of Compound A-1 in 3 ml of toluene was coated by spin coating at 1,000 rpm for 30 seconds and dried under vacuum for 1 hour at 60° C. to form a light emitting layer having a thickness of 80 nm.

Thus obtained substrate was attached in a vacuum vapor deposition apparatus and the pressure in the vacuum chamber was reduced by $4 \times 10^{-4}$ Pa and 10 nm of calcium as a buffer layer and 110 nm of aluminum as a cathode were deposited to prepare Organic Electroluminescent Element 1-1.

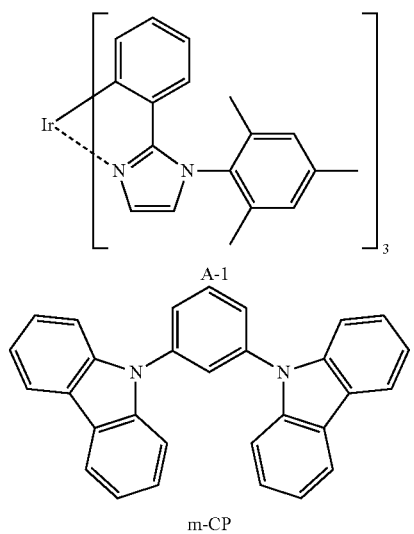

A-1 m-CP

<<Preparation of Organic Electroluminescent Elements 1-2 Through 1-5>>

Organic Electroluminescent Elements 1-2 Through 1-5 were prepared in the same manner as in Organic Electroluminescent Element 1-1 except that Compound A-1 used for formation of the light emitting layer was replaced by the compound having the partial structure represented by Formulas (1), (2) or (3) of the present invention as shown in the column of metal complex compound of Table 1.

<<Organic Electroluminescent Elements 1-1 Through 1-5>>

Figure 3:
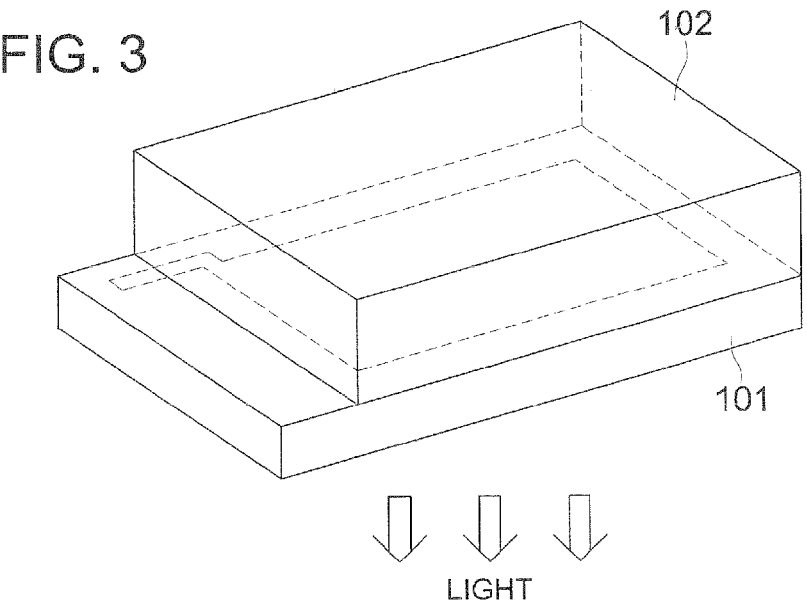
FIG. 3 is a schematic drawing of a lighting device.

On the occasion of evaluation of Organic Electroluminescent Elements 1-1 through 1-5, the non-light emitting side of each of the organic electroluminescent elements was covered with a glass case and a sealing glass plate having a thickness of 300 µm on which an epoxy type photo curable adhesive, Laxtruck LC0629B manufactured by Toagosei Co., Ltd., was applied was piled on the cathode and contacted with the transparent substrate plate, and then irradiated with UV rays to cure the adhesive to prepare a lighting device to be evaluated shown in FIGS. 3 and 4.

FIG. 3 shows a schematic drawing of the lighting device, in which the organic electroluminescent element 101 was covered by the glass cover 102. The sealing operation using the glass cover was carried out in nitrogen atmosphere (high purity nitrogen gas of not less than 99.999) in a glove box for preventing contact of the organic electroluminescent element 101 with air. FIG. 4 shows a cross section of the lighting device, in which 105 is the cathode, 106 is the electroluminescent layer and 107 is the glass substrate plate with the transparent electrode. Interior of the glass cover is filled by nitrogen gas 108 and moisture capturing agent 109 is provided.

<<External Quantum Efficiency>>

As to each of the prepared organic electroluminescent elements, the external quantum efficiency was determined when a constant electric current of 2.5 mA/cm² was applied at 23° C. in a dried nitrogen atmosphere. A spectral emission luminance meter CS-1000, manufactured by Konica Minolta Sensing Corp., was used for the determination.

<<Light Emission Lifetime>>

The time necessary for reducing by half the luminance of the emitted light just after the starting of light emission when the device was driven by a constant electric current of 2.5 mA/cm² at 23° C. in a dried nitrogen atmosphere was measured and the time was referred to as a half-lifetime ($\tau^{1/2}$) and used as an indicator of the life time. The spectral emission luminance meter CS-1000, manufactured by Konica Minolta Sensing Corp., was also used for the determination.

The measured results of the external quantum efficiency and the light emission lifetime of Organic Electroluminescent Elements 1-1 through 1-5 were relatively evaluated when the values of Organic Electroluminescent Elements 1-5 were each set at 100.

The obtained results are listed in Table 1.

TABLE 1

| Organic Element | Metal complex compound | External quantum efficiency | Lifetime | Remarks |
|---|---|---|---|---|
| 1-1 | A-1 | 100 | 100 | Comparative |
| 1-2 | 1-1 | 112 | 130 | Inventive |
| 1-3 | 1-13 | 121 | 142 | Inventive |
| 1-4 | 1-47 | 118 | 122 | Inventive |
| 1-5 | 1-52 | 109 | 186 | Inventive |

It is clear from Table 1 that the raising of the efficiency and lifetime are attained by the organic electroluminescent elements using the compound of the present invention containing the partial structure represented by Formulas (1), (2) or (3) compared with the organic electroluminescent element using the comparative compound.

Example 2

Preparation of Organic Electroluminescent Element 2-1

A glass substrate of 100 mm×100 mm×1.1 mm on which an ITO (indium tin oxide) layer of 100 nm was provided as an anode (NA45 manufactured by NH Techno Glass Corp.) was subjected to patterning and thus obtained transparent substrate plate having the ITO transparent anode was washed by ultrasonic treatment using isopropyl alcohol, dried by dried nitrogen gas and subjected to UV-ozone cleaning for 5 minutes.

The substrate was attached onto a spin coater and coated with a solution prepared by diluting poly(3,4-ethylenedioxythiophene)-polystyrene-sulfonate (PEDOT/PSS, Baytron P Al 4083 manufactured by Bayer) with purified water by 70 weight percent by spin coating at 3,000 rpm for 30 seconds and dried under vacuum for 1 hour at 200° C. to provide a positive hole injection layer with a thickness of 30 nm.

After the drying treatment, the substrate was attached again onto the spin coater and coated with a solution prepared by dissolving 60 mg of Compound A-2 in 6 ml of cyclohexane by spin coating at 1,000 rpm for 30 seconds (layer thickness of 40 nm) and dried for 1 hour at 60° C. under vacuum and then irradiated with UV rays for 5 minutes to form a positive hole transfer layer.

The substrate was attached onto the spin coater in the same manner as in the formation of the positive hole transfer layer and coated with a solution prepared by dissolving 60 mg of CPB and 3 mg of Compound 1-19 of the present invention in 6 ml of cyclohexane at 1,000 rpm for 30 seconds (layer thickness of 40 nm) and dried for 1 hour at 60° C. to form a light emitting layer.

The resultant substrate was fixed on a substrate holder of a vacuum vapor deposition apparatus and a molybdenum resistance heating boat containing 200 mg of Bathocuproine (BCP) and another molybdenum resistance heating boat containing 200 mg of $Alq_3$ were set in the vacuum vapor deposition apparatus.

After reducing the pressure in the vacuum chamber until $4 \times 10^{-4}$ Pa, the heating boat containing BCP was heated by applying electric current for depositing BCP on the light emitting layer at a deposition rate of 0.1 nm/sec to provide a positive hole blocking layer with a layer thickness of 10 nm.

Moreover, the heating boat containing $Alq_3$ was heated by applying electric current for depositing $Alq_3$ on the positive hole blocking layer at a deposition rate of 0.1 nm/sec to provide an electron transfer layer with a layer thickness of 40 nm. The temperature of the substrate on the occasion of the vapor deposition was room temperature.

After that, 0.5 nm of lithium fluoride and 110 nm of aluminum were vapor deposited to form a cathode. Thus Organic Electroluminescent Element 2-1 was prepared. Green light was emitted when electric current was applied to thus obtained device and it was confirmed that the device could be used as an organic electroluminescent display device.

Furthermore, organic electroluminescent elements were each prepared by replacing Compound 1-19 of the present invention used in Organic Electroluminescent Element 2-1 by Compound 1-2, 1-7, 1-11, 1-20, 1-33, 1-41, 1-55 and 1-56, respectively, which contain one of the partial structure represented by Formulas (1), (2) or (3), and the similar results were obtained.

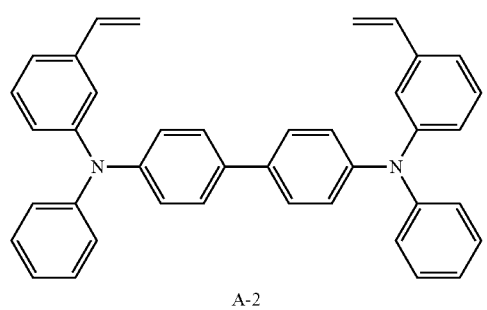

A-2

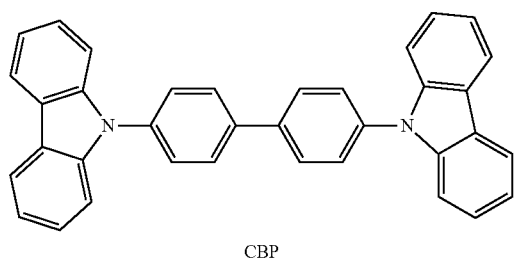

CBP

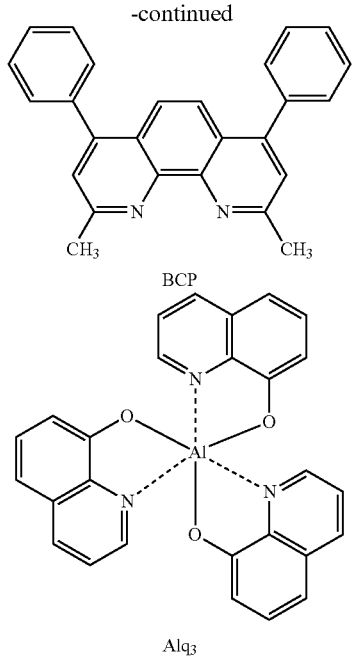

BCP $Alq_3$

Example 3

Preparation of Full-Color Display Apparatus (Blue Light Emission Organic Electroluminescent Element)
Organic Electroluminescent 1-2 prepared in Example 1 was used as a blue light emission Organic Electroluminescent Element 3-1 (Blue).

(Green Light Emission Organic Electroluminescent Element)
Green light emission Organic Electroluminescent Element 3-2 (Green) was prepared in the same manner as in Organic Electroluminescent Element 1-2 except that Compound 1-1 of the present invention was replaced by Compound 1-21 of the present invention.

(Red Light Emission Organic Electroluminescent Element)
Red light emission Organic Electroluminescent Element 3-3 (Red) was prepared in the same manner as in Organic Electroluminescent Element 1-2 except that Compound 1-1 of the present invention was replaced by Compound 1-55 of the present invention.

Figure 2:
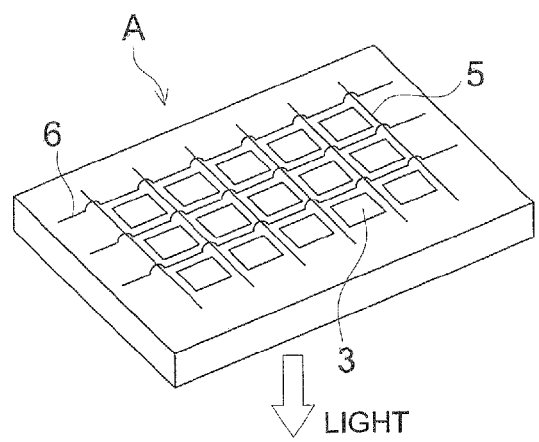
FIG. 2 is a schematic drawing of a display section.

An active matrix type full-color display apparatus having the constitution shown in FIG. 1 was prepared by arranging the red, green and blue light emission organic electroluminescent elements on a plane. In FIG. 2, the schematic drawing of displaying part A of the above-prepared displaying apparatus is only displayed. The apparatus has a wiring part including plural scanning lines 5, scanning lines 6 and the arranged plural pixels 3 (pixels each emitting light in red range, green range or blue range) on the same substrate, the scanning lines and the plural data lines are each made from an electro-conductive material and crossed at right angles in a lattice state and connected with the pixel at the crossing point (details are not displayed in the drawing). The plural pixels are driven by an active matrix system having the organic electroluminescent elements corresponding to each of the colors, a switching transistor as the active element and a driving transistor. The light emission device receives image data signals from the data line 6 and emits light corresponding to the received signals when scanning signals are applied from the scanning line 5. A full-color displaying apparatus was prepared by suitably arranging the red, green and blue pixels as above-mentioned.

It was continued by driving the above-prepared full-color displaying apparatus that a full-color displaying apparatus having high light emission efficiency and long light emission lifetime could be obtained.

Example 4

Preparation of White Lighting Device

White light emission Organic Electroluminescent Element 4-1 (White) was prepared in the same manner as in Organic Electroluminescent Element 1-2 except that Compound 1-1 of the present invention was replaced by a mixture of Compound 1-1 and Compound 1-51 of the present invention.

When thus obtained Organic Electroluminescent Element 4-1 was evaluated, the non light emission side of device was covered by a glass case in the same manner as in Example 1 to prepare an lighting device. The lighting device could be used as a thin-type lighting device having high light emission efficiency and low light emission lifetime.

Example 5

Organic Electroluminescent Element 5-1 was prepared in the same manner as in Organic Electroluminescent Element 1-1 except that Compound m-CP used in the light emitting layer was replaced by Compound 2-2. Moreover, Organic Electroluminescent Elements 5-2 through 5-5 were prepared in the same manner as in Organic Electroluminescent Element 5-1 except that Compound 1 used for forming the light emitting layer was replaced by a compound having one of the partial structures represented by Formulas (1), (2) or (3) which are shown in the column of metal complex compound of Table 2.

Thus obtained Organic Electroluminescent Elements 5-1 through 5-5 were evaluated in the same manner as in Example 1. The evaluation results are shown in Table 2.

TABLE 2

| Organic element | Metal complex compound | External quantum efficiency | Lifetime | Remarks |
|---|---|---|---|---|
| 5-1 | A-1 | 100 | 100 | Comparative |
| 5-2 | 1-1 | 133 | 180 | Inventive |
| 5-3 | 1-13 | 124 | 165 | Inventive |
| 5-4 | 1-66 | 141 | 142 | Inventive |
| 5-5 | 1-67 | 122 | 121 | Inventive |

It is clear from Table 2 that the raising of the efficiency and lifetime are attained by the organic electroluminescent elements using the compound of the present invention containing the partial structure represented by Formulas (1), (2) or (3) compared with the organic electroluminescent element using the comparative compound.

What we claim is:

1. An organic electroluminescent element comprising a compound having a partial structure represented by Formula (3) in the molecule:

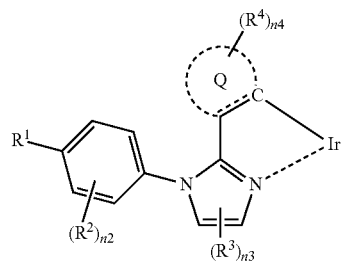

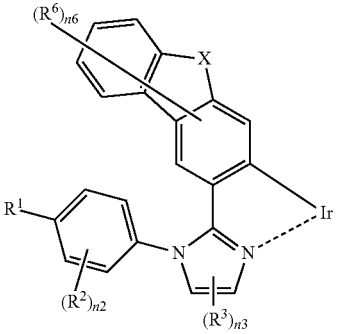

Formula (3)

wherein $R^1$ is an aromatic hydrocarbon group or an aromatic heterocyclic group substituted by a substituent having 4 to 20 carbon atoms a formula weight of 70 to 350, and substituent is selected from the group consisting of:
an alkyl group, an alkoxyl group, a cycloalkyl group, an aryl group and an aromatic heterocyclic group;
$R^2$, $R^3$ and $R^6$ are each independently a substituent; n2 is an integer of 0 to 4; n3 is an integer of 0 to 2; and n6 an integer of 0 to 6; and X is a chalcogen atom.

2. The organic electroluminescent element of claim 1, wherein $R^6$ is a group selected from the group consisting of an alkyl group, a cycloalkyl group, an alkenyl group, an alkynyl group, an aromatic hydrocarbon ring group, an aromatic heterocyclic group, a heterocyclic group and an alkoxyl group.

3. The organic electroluminescent element comprising an organic layer which contains the compound described in claim 1.

4. The organic electroluminescent element of claim 3, wherein the organic layer is a light emission layer.

5. The organic electroluminescent element of claim 3, wherein the organic layer is formed by a wet process.

6. A display device having the organic electroluminescent element of claim 1.

7. A lighting device comprising the organic electroluminescent element of claim 1.

* * * * *